(12) United States Patent
Felix et al.

(10) Patent No.: US 9,433,439 B2
(45) Date of Patent: Sep. 6, 2016

(54) RADIOLUCENT STABILIZING ROD WITH RADIOPAQUE MARKER

(75) Inventors: Brent A. Felix, Sandy, UT (US); David N. McKean, Bountiful, UT (US); David A. Hershgold, Draper, UT (US)

(73) Assignee: Innovasis, Inc., Salt Lake City, UT (US)

( * ) Notice: Subject to any disclaimer, the term of this patent is extended or adjusted under 35 U.S.C. 154(b) by 195 days.

(21) Appl. No.: 12/557,081

(22) Filed: Sep. 10, 2009

(65) Prior Publication Data

US 2011/0060365 A1 Mar. 10, 2011

(51) Int. Cl.
*A61B 17/70* (2006.01)
*A61B 17/00* (2006.01)

(52) U.S. Cl.
CPC ....... *A61B 17/7002* (2013.01); *A61B 17/7011* (2013.01); *A61B 2017/00526* (2013.01)

(58) Field of Classification Search
CPC ...................................... A61B 17/70–17/7031
USPC .................................................. 606/246–278
See application file for complete search history.

(56) References Cited

U.S. PATENT DOCUMENTS

| | | |
|---|---|---|
| 1,828,287 A | 10/1931 | Macbean |
| 2,405,909 A | 8/1946 | Smith |
| 3,455,360 A | 7/1969 | Leon |
| 4,265,981 A | 5/1981 | Campbell |
| 4,307,979 A | 12/1981 | Killmeyer |
| 4,329,743 A | 5/1982 | Alexander et al. |
| 4,403,606 A | 9/1983 | Woo et al. |
| 4,512,038 A | 4/1985 | Alexander et al. |
| 4,623,290 A | 11/1986 | Kikuzawa et al. |
| 4,778,637 A | 10/1988 | Adams et al. |
| 4,863,330 A | 9/1989 | Olez et al. |
| 4,863,470 A | 9/1989 | Carter |
| 5,084,051 A | 1/1992 | Tormala et al. |
| 5,127,783 A | 7/1992 | Moghe et al. |
| 5,209,888 A | 5/1993 | Shimada et al. |
| 5,246,655 A | 9/1993 | Mitchell et al. |
| 5,366,773 A | 11/1994 | Schroll et al. |
| 5,466,237 A | 11/1995 | Byrd, III et al. |
| 5,474,555 A | 12/1995 | Puno et al. |
| 5,540,870 A | 7/1996 | Quigley |
| 5,676,146 A | 10/1997 | Scarborough |

(Continued)

FOREIGN PATENT DOCUMENTS

| | | |
|---|---|---|
| DE | 44 43 051 A1 | 10/1996 |
| DE | 100 65 799 C1 | 4/2002 |

(Continued)

OTHER PUBLICATIONS

PCT/US2011/024935, May 23, 2011, International Search Report and Written Opinion.

(Continued)

*Primary Examiner* — Eduardo C Robert
*Assistant Examiner* — Michelle C Eckman
(74) *Attorney, Agent, or Firm* — Workman Nydegger

(57) ABSTRACT

A stabilizing rod includes an elongate shaft extending between a proximal end and an opposing distal end. The shaft is comprised of a radiolucent material and bounds a passageway that at least partially extends between the proximal end and the distal end. A core is disposed within the passageway of the shaft. The core can be comprised of a radiopaque material. The stabilizing rod can also include a radiopaque marker disposed on or within the shaft.

31 Claims, 13 Drawing Sheets

(56) References Cited

U.S. PATENT DOCUMENTS

| | | |
|---|---|---|
| 5,807,051 A | 9/1998 | Heminger |
| 5,951,556 A | 9/1999 | Faccioli et al. |
| 6,059,769 A | 5/2000 | Lunn et al. |
| 6,063,090 A | 5/2000 | Schlapfer |
| 6,099,528 A * | 8/2000 | Saurat .................... 606/254 |
| 6,113,826 A | 9/2000 | Tajima et al. |
| 6,117,173 A | 9/2000 | Taddia et al. |
| 6,174,329 B1 | 1/2001 | Callol et al. |
| 6,203,568 B1 | 3/2001 | Lombardi et al. |
| 6,214,921 B1 | 4/2001 | Bluett et al. |
| 6,248,105 B1 | 6/2001 | Schlapfer et al. |
| 6,280,442 B1 | 8/2001 | Barker et al. |
| 6,302,630 B1 | 10/2001 | Grant |
| 6,340,367 B1 | 1/2002 | Stinson et al. |
| 6,342,055 B1 | 1/2002 | Eisermann et al. |
| 6,371,957 B1 | 4/2002 | Amrein et al. |
| 6,423,067 B1 | 7/2002 | Eisermann |
| 6,471,705 B1 | 10/2002 | Biedermann et al. |
| 6,565,567 B1 | 5/2003 | Haider |
| 6,575,975 B2 | 6/2003 | Brace et al. |
| 6,641,586 B2 | 11/2003 | Varieur |
| 6,660,004 B2 | 12/2003 | Barker et al. |
| 6,679,883 B2 | 1/2004 | Hawkes et al. |
| 6,712,852 B1 | 3/2004 | Chung et al. |
| 6,740,086 B2 | 5/2004 | Richelsoph |
| 6,837,905 B1 | 1/2005 | Lieberman |
| 6,955,513 B2 | 10/2005 | Niku |
| 6,974,480 B2 | 12/2005 | Messerli et al. |
| 7,150,594 B2 | 12/2006 | Keener |
| 7,169,150 B2 | 1/2007 | Shipp et al. |
| 7,192,447 B2 | 3/2007 | Rhoda |
| 7,235,079 B2 | 6/2007 | Jensen et al. |
| 7,235,290 B2 | 6/2007 | Vallittu et al. |
| 7,273,481 B2 | 9/2007 | Lombardo et al. |
| 7,318,825 B2 | 1/2008 | Butler et al. |
| 7,524,190 B2 | 4/2009 | Levin |
| 7,766,942 B2 * | 8/2010 | Patterson et al. ............. 606/261 |
| 7,966,711 B2 | 6/2011 | Keener |
| 7,988,710 B2 * | 8/2011 | Jahng et al. .................. 606/254 |
| 7,998,180 B2 | 8/2011 | Erickson et al. |
| 8,267,978 B2 | 9/2012 | Lindemann et al. |
| 8,475,505 B2 | 7/2013 | Nebosky et al. |
| 2002/0123751 A1 | 9/2002 | Fallin |
| 2002/0133158 A1 | 9/2002 | Saint Martin |
| 2003/0078583 A1 | 4/2003 | Biedermann et al. |
| 2004/0034430 A1 | 2/2004 | Faiahee |
| 2004/0127904 A1 | 7/2004 | Konieczynski et al. |
| 2004/0143265 A1 | 7/2004 | Landry et al. |
| 2004/0199251 A1 | 10/2004 | McCombe et al. |
| 2004/0210226 A1 * | 10/2004 | Trieu .................... A61F 2/442 606/232 |
| 2004/0210316 A1 | 10/2004 | King et al. |
| 2004/0215195 A1 | 10/2004 | Shipp et al. |
| 2004/0243129 A1 | 12/2004 | Moumene et al. |
| 2005/0187550 A1 | 8/2005 | Grusin |
| 2005/0187555 A1 | 8/2005 | Biedermann et al. |
| 2005/0203516 A1 | 9/2005 | Biedermann et al. |
| 2005/0203517 A1 | 9/2005 | Jahng et al. |
| 2005/0203519 A1 | 9/2005 | Harms et al. |
| 2005/0216081 A1 | 9/2005 | Taylor |
| 2005/0228388 A1 | 10/2005 | Brodke et al. |
| 2005/0228479 A1 | 10/2005 | Pavcnik et al. |
| 2006/0041259 A1 * | 2/2006 | Paul .................... A61B 17/7023 606/250 |
| 2006/0084986 A1 | 4/2006 | Grinberg et al. |
| 2006/0085072 A1 | 4/2006 | Funk et al. |
| 2006/0089644 A1 | 4/2006 | Felix |
| 2006/0142758 A1 * | 6/2006 | Petit .................... A61B 17/7028 606/261 |
| 2006/0149228 A1 * | 7/2006 | Schlapfer et al. ............. 606/61 |
| 2006/0195093 A1 * | 8/2006 | Jahng ........................ 606/61 |
| 2006/0200140 A1 | 9/2006 | Lange |
| 2006/0235410 A1 | 10/2006 | Ralph et al. |
| 2006/0247638 A1 * | 11/2006 | Trieu .................... A61B 17/7031 606/246 |
| 2006/0276788 A1 | 12/2006 | Berry et al. |
| 2007/0123879 A1 | 5/2007 | Songer et al. |
| 2007/0156145 A1 | 7/2007 | Demakas et al. |
| 2007/0190230 A1 * | 8/2007 | Trieu et al. .................. 427/2.24 |
| 2007/0233071 A1 | 10/2007 | Dewey et al. |
| 2007/0233073 A1 * | 10/2007 | Wisnewski et al. ............ 606/61 |
| 2007/0250167 A1 | 10/2007 | Bray et al. |
| 2007/0270851 A1 | 11/2007 | Erickson et al. |
| 2008/0033437 A1 | 2/2008 | Shipp et al. |
| 2008/0065070 A1 | 3/2008 | Freid et al. |
| 2008/0077133 A1 | 3/2008 | Schulze et al. |
| 2008/0082103 A1 * | 4/2008 | Hutton et al. ................. 606/73 |
| 2008/0083613 A1 | 4/2008 | Oi et al. |
| 2008/0086127 A1 * | 4/2008 | Patterson ........... A61B 17/7011 606/86 R |
| 2008/0086129 A1 | 4/2008 | Lindemann |
| 2008/0091214 A1 | 4/2008 | Richelsoph |
| 2008/0097432 A1 | 4/2008 | Schulze |
| 2008/0125777 A1 * | 5/2008 | Veldman et al. ............... 606/61 |
| 2008/0154306 A1 | 6/2008 | Heinz |
| 2008/0154367 A1 * | 6/2008 | Justis et al. ................ 623/11.11 |
| 2008/0243185 A1 | 10/2008 | Felix et al. |
| 2009/0082810 A1 | 3/2009 | Bhatnagar et al. |
| 2009/0093819 A1 | 4/2009 | Joshi |
| 2009/0093844 A1 * | 4/2009 | Jackson ........................ 606/254 |
| 2009/0112265 A1 * | 4/2009 | Hudgins et al. ............. 606/254 |
| 2009/0118767 A1 * | 5/2009 | Hestad et al. ................ 606/279 |
| 2009/0163955 A1 * | 6/2009 | Moumene et al. ........... 606/257 |
| 2009/0234388 A1 * | 9/2009 | Patterson et al. ............. 606/246 |
| 2009/0240284 A1 * | 9/2009 | Randol ............... A61B 17/7004 606/254 |
| 2009/0248083 A1 * | 10/2009 | Patterson et al. ............. 606/279 |
| 2009/0275983 A1 * | 11/2009 | Veldman et al. ............. 606/258 |
| 2009/0287251 A1 * | 11/2009 | Bae et al. ..................... 606/254 |
| 2009/0326582 A1 * | 12/2009 | Songer et al. ................ 606/255 |
| 2010/0042215 A1 | 2/2010 | Stalcup et al. |
| 2010/0063550 A1 | 3/2010 | Felix |
| 2010/0082064 A1 * | 4/2010 | Chun et al. ................... 606/246 |
| 2010/0087863 A1 * | 4/2010 | Biedermann et al. ........ 606/261 |
| 2010/0114167 A1 * | 5/2010 | Wilcox et al. ............... 606/250 |
| 2010/0160967 A1 * | 6/2010 | Capozzoli ..................... 606/256 |
| 2010/0211104 A1 * | 8/2010 | Moumene et al. ........... 606/257 |
| 2010/0211105 A1 * | 8/2010 | Moumene et al. ........... 606/258 |
| 2011/0054534 A1 * | 3/2011 | Biedermann et al. ........ 606/254 |
| 2011/0112321 A1 | 9/2011 | Felix |
| 2012/0109207 A1 * | 5/2012 | Trieu ............................ 606/254 |

FOREIGN PATENT DOCUMENTS

| | | |
|---|---|---|
| FR | 2 899 787 | 10/2007 |
| GB | 2 294 399 | 1/1996 |
| JP | 2005-270250 | 10/2005 |
| JP | 2006-187658 | 7/2006 |
| JP | 2007-307368 | 11/2007 |
| WO | WO 94/04095 A1 | 3/1994 |
| WO | WO 2007/127845 | 11/2007 |

OTHER PUBLICATIONS

PCT/US2009/056508, Feb. 19, 2010, International Search Report and Written Opinion.

S. Kawahara et al., *Clinical Imaging Diagnosis of Implant Materials for Breast Augmentation*, Ann Plast Surg., Jul. 2006; 57(1), pp. 6-12.

*VLS System Variable Locking Screw*, Interpore Cross International, 2001.

EBI Spine Systems, *EBI Ωmega21 Spinal Fixation System*, Surgical Technique, published at least as early as Sep. 1, 2006.

*Click'X Top Loading System*, Technique Guide, Synthes Spine 2003.

*Synergy IQ, Low Back Surgical Technique*, Interpore Cross International, 2003.

Office Action dated Jan. 19, 2012, issued in U.S. Appl. No. 12/719,765, filed Mar. 8, 2010.

PCT/US2010/048243, Sep. 9, 2010, International Search Report and Written Opinion issued Nov. 10, 2010.

Office Action dated May 3, 2013, issued in U.S. Appl. No. 13/063,605, filed Mar. 11, 2011.

(56) References Cited

OTHER PUBLICATIONS

Final Office Action dated May 9, 2012, issued in U.S. Appl. No. 12/719,765, filed Mar. 8, 2010.
Office Action dated Aug. 17, 2012, issued in U.S. Appl. No. 12/719,765, filed Mar. 8, 2010.
Office Action dated Jul. 10, 2012, issued in U.S. Appl. No. 12/208,986, filed Sep. 11, 2008.
Final Office Action dated Dec. 14, 2012, issued in U.S. Appl. No. 12/208,986, filed Sep. 11, 2008.
Office Action issued dated Feb. 16, 2013, issued in Chinese Application No. 200980144925.0, filed Sep. 11, 2011.
Office Action dated Sep. 14, 2011 issued in EP Application No. 09792417.9, filed Sep. 11, 2011.
Office Action dated Oct. 15, 2013, issued in JP 2011-526971, filed May 16, 2011.
Office Action dated Nov. 18, 2013, issued in U.S. Appl. No. 12/719,765, filed Mar. 8, 2010.

* cited by examiner

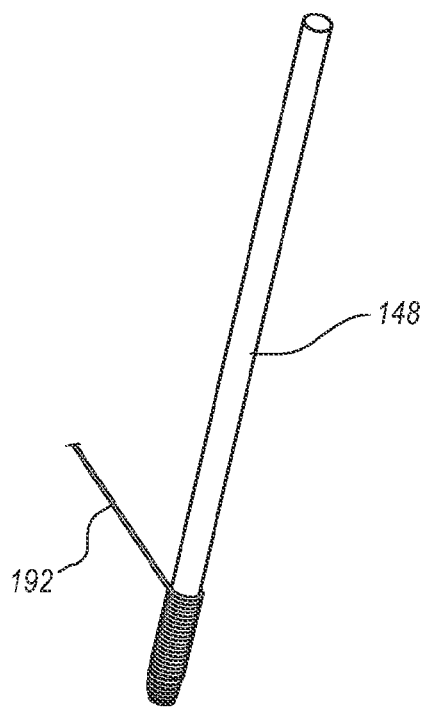 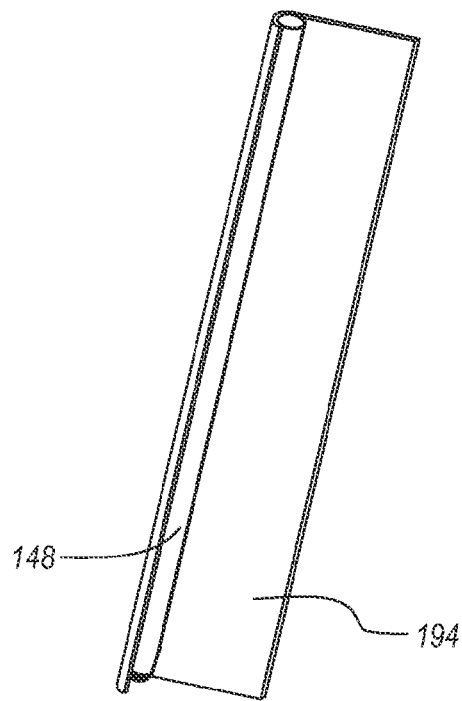
FIG. 14  FIG. 15
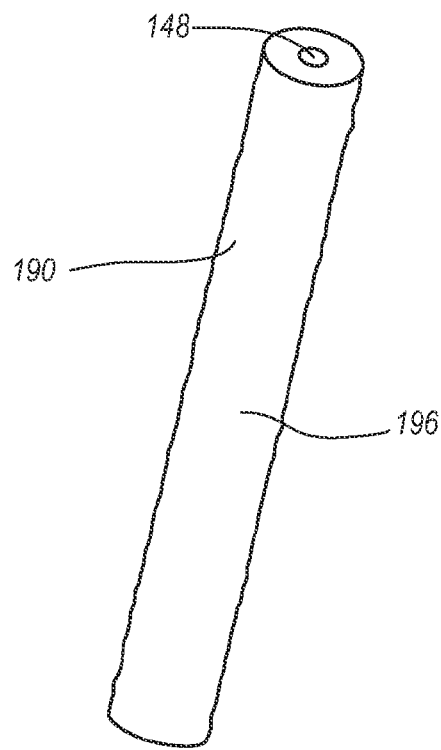
FIG. 16

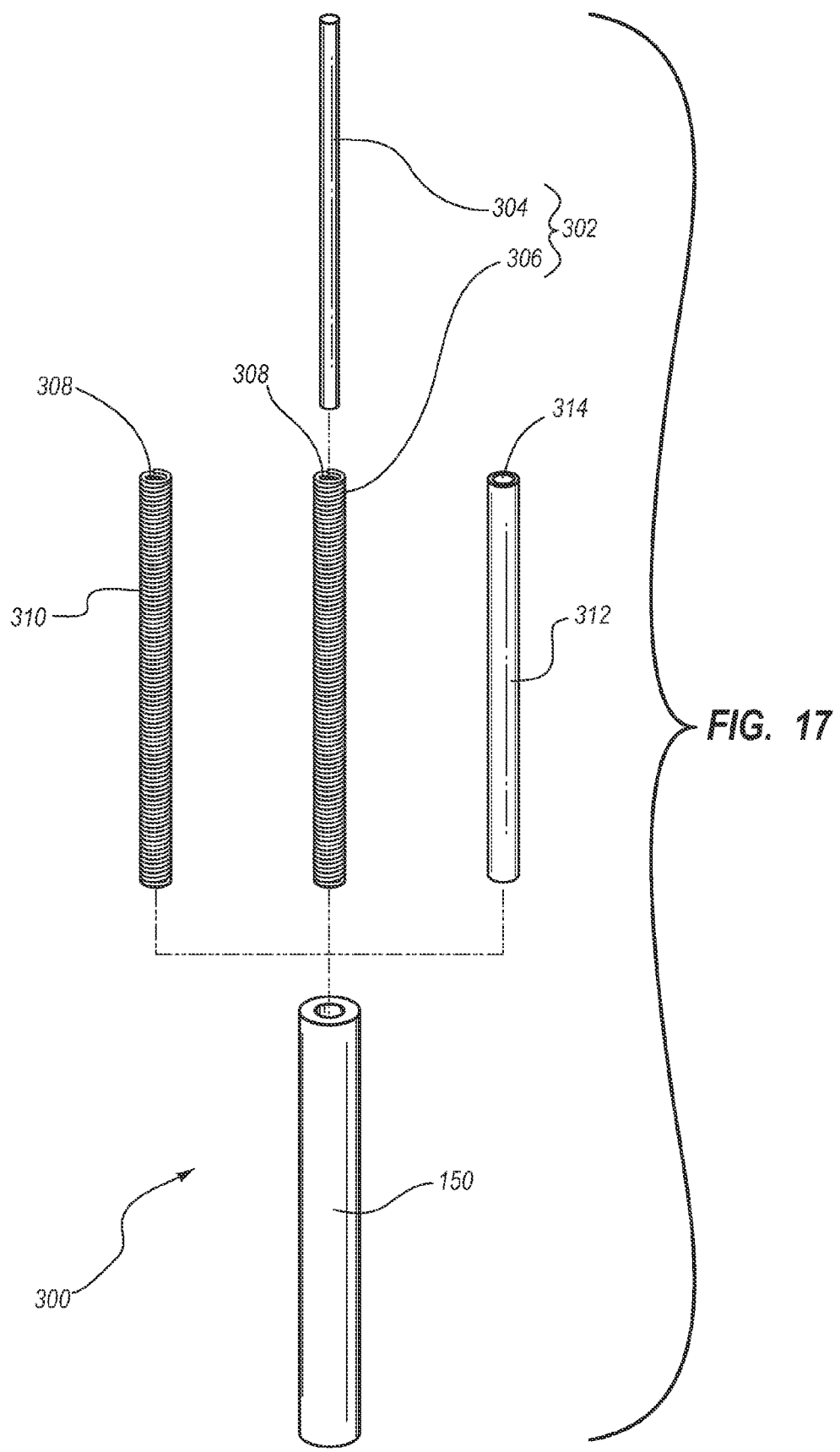

RADIOLUCENT STABILIZING ROD WITH RADIOPAQUE MARKER

CROSS-REFERENCE TO RELATED APPLICATIONS

Not Applicable.

BACKGROUND OF THE INVENTION

1. The Field of the Invention

The present invention relates to systems and components for stabilizing adjacent vertebrae of the spine or other adjacent bones and, more specifically, it relates to radiolucent stabilizing rods and screw systems used in stabilizing adjacent vertebrae.

2. The Relevant Technology

Spinal stabilizing systems are commonly used for adjusting or stabilizing adjacent vertebrae of a spine. A typical spinal stabilizing system includes bone screws that secure to the vertebrae and stabilizing rods that extend between the bone screws. For example, in one conventional procedure a first bone screw is screwed into a first vertebra while a second bone screw is screwed into an adjacent second vertebra. A stabilizing rod is then secured between the bone screws so as to fix the adjacent vertebrae relative to each other. Bone screws can be positioned on each side of each vertebra and can be positioned in any number of consecutive vertebrae with one or more stabilizing rods extending between the different bone screws.

A conventional bone screw comprises a threaded shaft having a collar mounted on the end thereof. The threaded shaft is screwed into the vertebrae and the stabilizing rod is received within the collar and secured therein. To be strong enough to handle the stresses placed upon them, the bone screws and stabilizing rods are typically made of titanium or some other high strength, biocompatible metal. As a result of being made of metal, a physician is able to view the bone screws and stabilizing rods using X-ray photographs during and after implantation.

However, the metal bone screws and stabilizing rods also block the X-rays and prevent them from passing through the body. As a result, the metal bone screws and stabilizing rods obscure adjacent bone and other X-ray viewable internal structures surrounding the area, thereby preventing the physician from viewing those structures on an X-ray photograph. This screening can limit a physician's ability to ensure proper placement/orientation of the bone screws and stabilizing rods relative to the surrounding bone structure. Such screening can also hamper the diagnoses and treatment of problems that arise near the location of the bone screws and stabilizing rods after the bone screws and stabilizing rods have been implanted.

Accordingly, what is needed are spinal stabilizing systems, including stabilizing rods, that overcome some or all of the above disadvantages.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 14 is a perspective view of impregnated fibers being wound on a core of a stabilizing rod according to one embodiment;

FIG. 15 is a perspective view of sheets of fibers being wound on a core of a stabilizing rod according to one embodiment;

FIG. 16 is a perspective view of a blank that is formed during manufacture of a stabilizing rod according to one embodiment; and FIG. 17 is a perspective view showing alternative embodiments of a stabilizing rod having tubular cores.

DETAILED DESCRIPTION OF THE PREFERRED EMBODIMENTS

Figure 1:
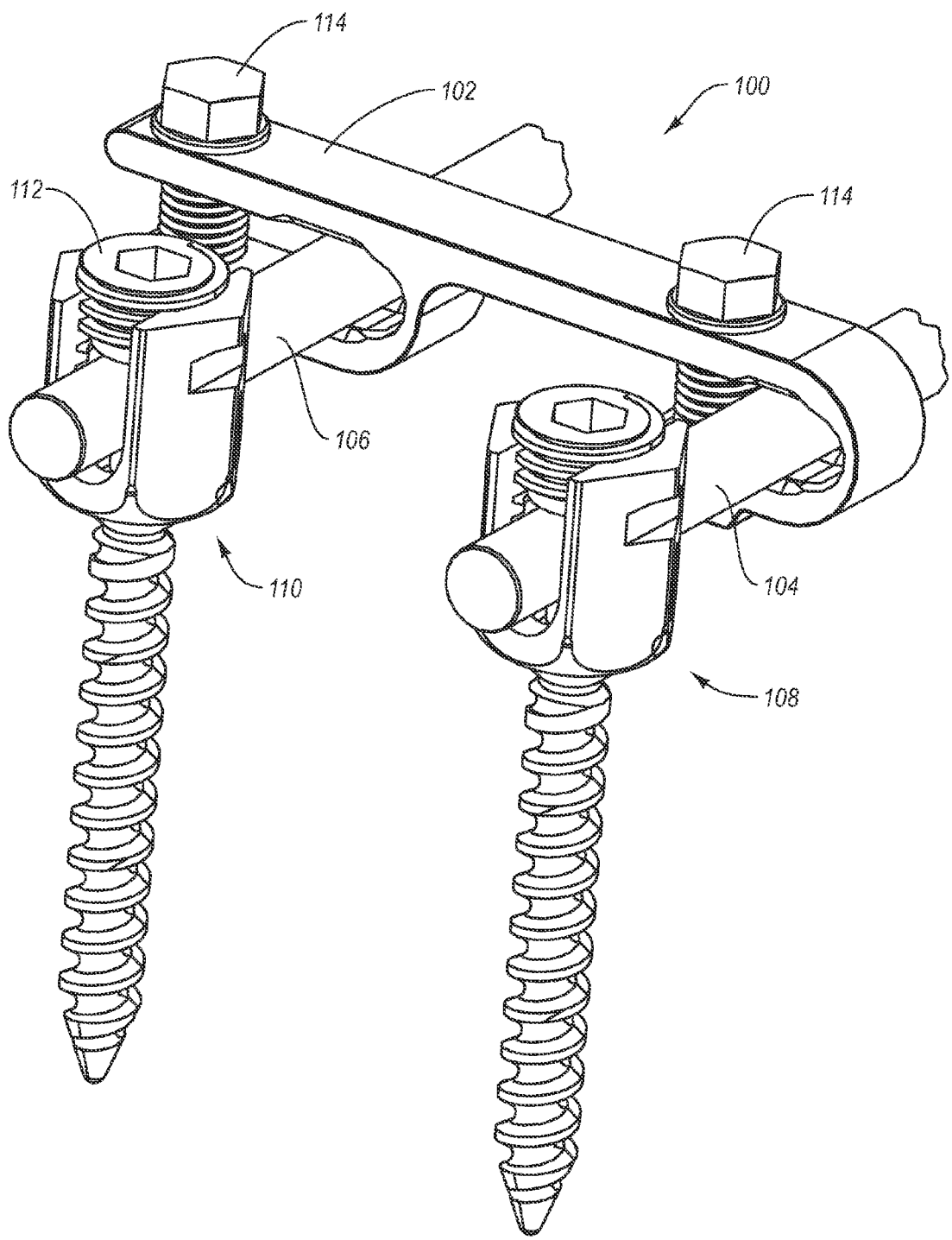
FIG. 1 is a perspective view of a spinal stabilizing system according to one embodiment.

Depicted in FIG. 1 is one embodiment of a spinal stabilizing system 100 incorporating features of the present invention. In one embodiment, spinal stabilizing system 100 can be used for stabilizing adjacent vertebrae of a spine as part of a procedure for fusing together the adjacent vertebrae. Spinal stabilizing system 100 can also be used for stabilizing a series of consecutive vertebrae for manipulation of the spine to correct spinal deformities such as scoliosis. It is appreciated that spinal stabilizing system 100 and/or discrete elements thereof can also be used in other procedures for anchoring, manipulating, and/or stabilizing various bones.

Spinal stabilizing system 100 generally comprises a cross link 102 to which a first stabilizing rod 104 and a spaced apart second stabilizing rod 106 can be rigidly secured thereto. System 100 also includes a first bone screw 108 that can be rigidly mounted on first stabilizing rod 104 and a second bone screw 110 that can be rigidly mounted on second stabilizing rod 106.

Although FIG. 1 depicts only one bone screw being mounted to each stabilizing rod, it is appreciated that the stabilizing rods can be any desired length and that spinal stabilizing system 100 typically includes at least two bone screws for mounting on each stabilizing rod. For example, a typical spinal stabilizing system 100 will include four bone screws where two bone screws are secured on opposing medial and lateral sides of a first vertebrae and the other two bone screws are secured on opposing medial and lateral sides of an adjacent second vertebrae. The first stabilizing rod is secured to and extends between the medially placed bone screws and the second stabilizing rod is secured to and extends between the laterally placed bone screws. The cross link 102 is then secured between the two stabilizing rods, thereby rigidly fixing the two adjacent vertebrae. Where it is needed to fix or otherwise manipulate three or more vertebra, three or more pairs of bone screws can be secured on opposing sides of any number of consecutive vertebrae and secured to the stabilizing rods. Furthermore, if needed, two or more cross links can be secured between the stabilizing rods at spaced apart locations along the stabilizing rods.

In another embodiment of spinal stabilizing system 100, it is appreciated that the system can be designed to only stabilize the medial or lateral sides of adjacent vertebrae. For example, system 100 can comprise two or more bone screws 108 that are designed for placement on the lateral side of adjacent vertebra. A single stabilizing rod 104 would secure to and extend between the two or more bone screws 108. In this embodiment, system 100 does not include cross link 102 or the second stabilizing rod 106. Other configurations for system 100, as is known in the art, can also be used.

Figure 2:
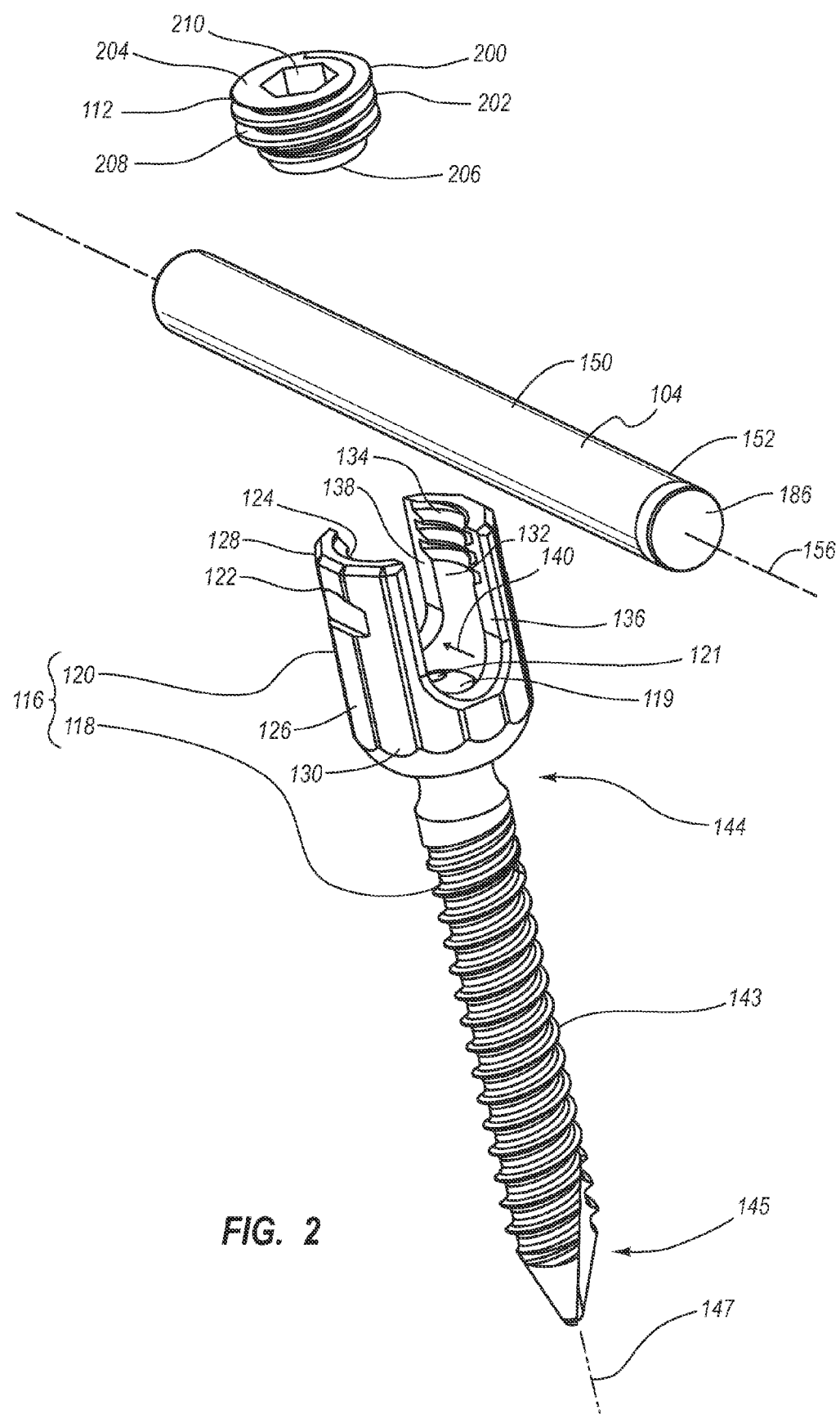
FIG. 2 is an exploded perspective view of a bone screw and accompanying stabilizing rod according to one embodiment.

Depicted in FIG. 2 is one embodiment of a bone screw 116 that can be used as bone screw 108 or 110 or can otherwise be used as part of spinal stabilizing system 100. Bone screw 116 comprises an elongated, threaded shaft 118 and a collar 120 mounted on an end thereof. Collar 120 can be rigidly attached to or integrally formed with shaft 118 to form a fixed bone screw. Conversely, shaft 118 can have a head 119 and, as in the depicted embodiment, collar 120 can be pivotally attached to shaft 118 using the head 119 to form a polyaxial bone screw, as discussed below.

Collar 120 comprises a tubular side wall 122 having an interior surface 124 and an exterior surface 126 that each extend between a first end 128 and an opposing second end 130. Interior surface 124 bounds a longitudinal passage 132 that longitudinally extends through collar 120. Internal threads 134 are formed on interior surface 124 at or toward first end 128.

Figure 3:
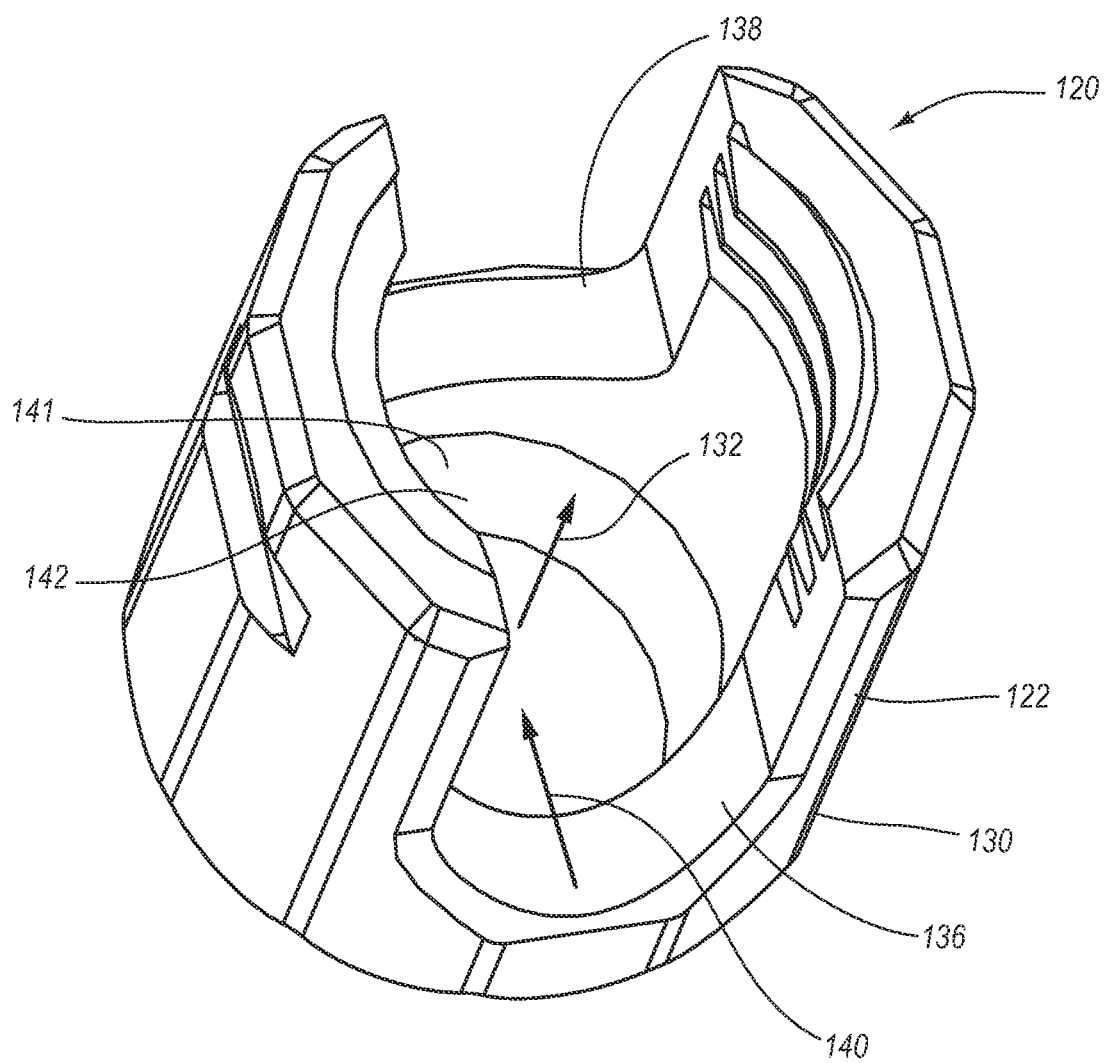
FIG. 3 is a perspective view of the collar of the bone screw shown in FIG. 2.

Turning to FIG. 3, side wall 122 is formed having a pair of channels 136 and 138 that are disposed on opposing sides of side wall 122 and that transversely extend through side wall 122. In the embodiment depicted, channels 136 and 138 each have a substantially U-shaped configuration. Other channel shapes can also be used. Channels 136 and 138 form a portion of a transverse passage that transversely extends through collar 120, as identified by arrow 140, so as to intersect with the longitudinal passage that also extends through collar 120, as identified by arrow 132. Each channel 136 and 138 is configured so that stabilizing rod 104 can be received therein as stabilizing rod 104 is placed within the transverse passage 140.

As also depicted in FIG. 3, collar 120 further comprises a shoulder 141 that radially inwardly projects from second end 130 of side wall 122 so as to encircle longitudinal passage 132. Shoulder 141 has a tapered interior surface that forms an annular seat 142. In alternative embodiments, seat 142 need not completely encircle passage 132. Seat 142 can also comprise two or more spaced apart portions.

Returning to FIG. 2, shaft 118 has a threaded exterior surface 143 extending between a first end 144 and an opposing second end 145. Shaft 118 also includes an enlarged head 119 disposed on first end 144. Although not required, in the embodiment depicted, head 119 has a substantially spherical configuration. It is also noted that shaft 118 has a central longitudinal axis 147 extending therethrough which axis 147 passes through head 119. A socket 121 or other type of engaging member or recess adapted to receive a driver can be disposed on the top surface of head 119.

During assembly of bone screw 116, second end 145 of shaft 118 is passed down through longitudinal passage 132 of collar 120. Head 119 of shaft 118, however, has a maximum diameter that is greater than the minimum diameter of longitudinal passage 132 extending through seat 142 of collar 120. As such, head 119 of shaft 118 rests on seat 142 of collar 120 and is prevented from passing through longitudinal passage 132. See, e.g., FIG. 7, which shows another embodiment of a collar 216 that incorporates the same seat/head interface. As a result of the spherical configuration of head 119 and the tapered sloping of seat 142, head 119 can freely slide on seat 142 such that shaft 118 and collar 120 can freely pivot relative to each other.

A fastener 112 can be used to secure stabilizing rod 104 to bone screw 116. Fastener 112 comprises a locking screw 200 having an encircling side wall 202 that extends between a top end face 204 and an opposing bottom end face 206. Radially outwardly projecting from side wall 202 of locking screw 200 so as to encircle locking screw 200 are one or more helical threads 208. Threads 208 of locking screw 200 are configured to threadedly engage with internal threads 134 of collar 120. A socket 210 or other type of engaging member or recess adapted to receive a driver can be disposed on top surface 204 of locking screw 200.

Fastener 112 is threaded into threads 134 formed on interior surface 124 of collar 120 to secure stabilizing rod 104 to bone screw 116 within channels 136 and 138 of collar 120. That is, once stabilizing rod 104 is disposed within the transverse passage of collar 120, locking screw 200 is screwed into collar 120 so that bottom end face 206 of locking screw 200 presses against stabilizing rod 104, which in turn causes stabilizing rod 104 to press against head 119 of shaft 118. In turn, head 119 is pressed into seat 142 of collar 120 so as to lock shaft 118 relative to collar 120.

Figure 4:
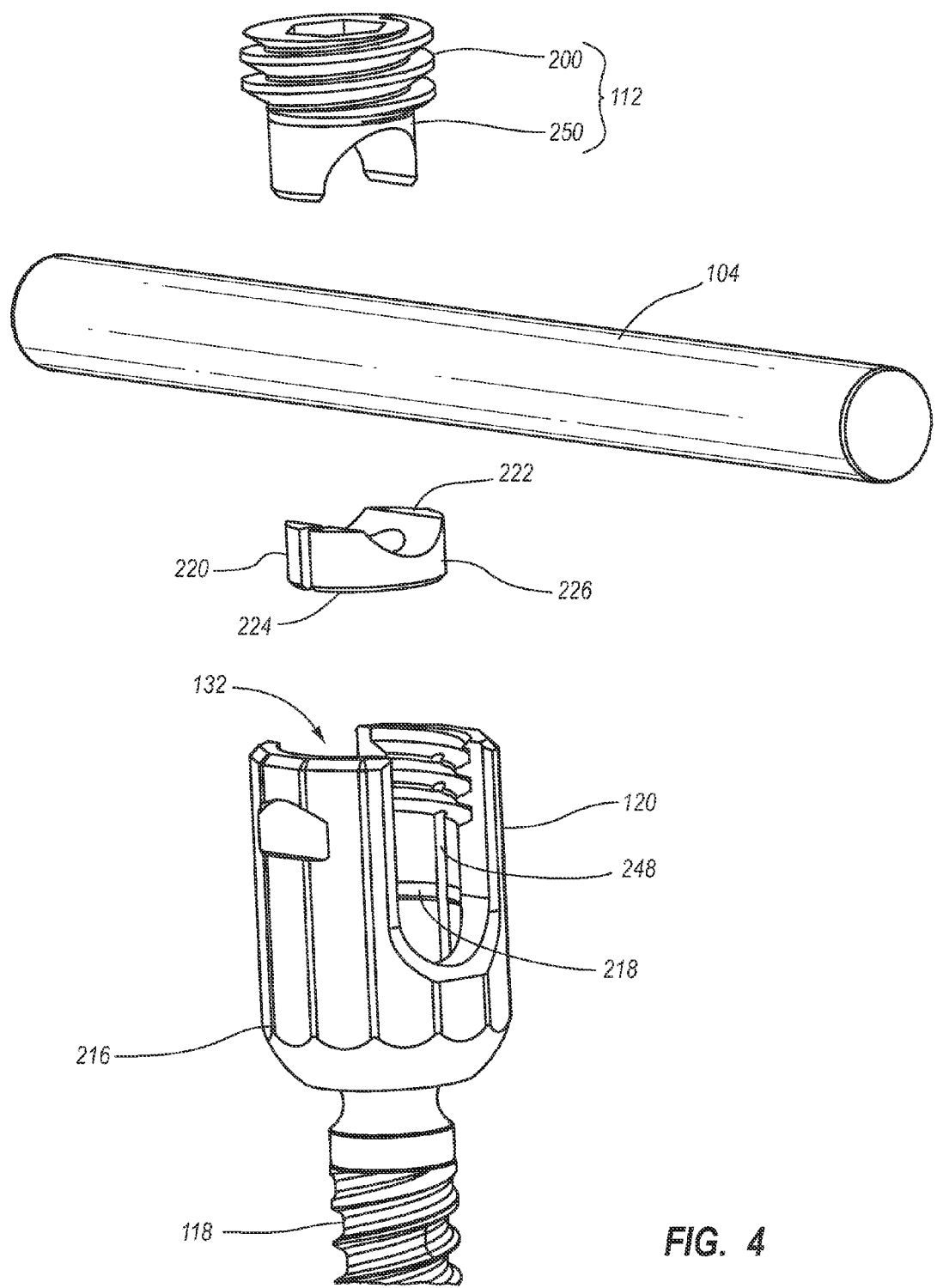
FIG. 4 is an exploded perspective view of a bone screw and accompanying stabilizing rod according to another embodiment.

In some embodiments a saddle is used to help distribute the clamping forces around stabilizing rod 104. For example, as depicted in FIG. 4, a saddle 220 can be positioned between shaft 118 and stabilizing rod 104 such that when fastener 112 is threaded into collar 120, stabilizing rod 104 presses against saddle 220, which in turn presses against head 119 of shaft 118. To be able to retain saddle 220 within passage 132 in a particular positioning arrangement, the collar can also include one or more channels or lips. For example, the embodiment depicted in FIG. 4 includes a collar 216 having a channel 248 formed on interior surface 124. Channel 248 is generally aligned with longitudinal passage 132 and is designed to receive a key formed on saddle 220, as discussed in more detail below. Furthermore, collar 216 also includes an inwardly projecting annular lip 218 formed on interior surface 124 that at least partially encircles longitudinal passage 132. Lip 218 is sized so as to have a slightly smaller diameter than the general diameter of interior surface 124.

Figure 5A:
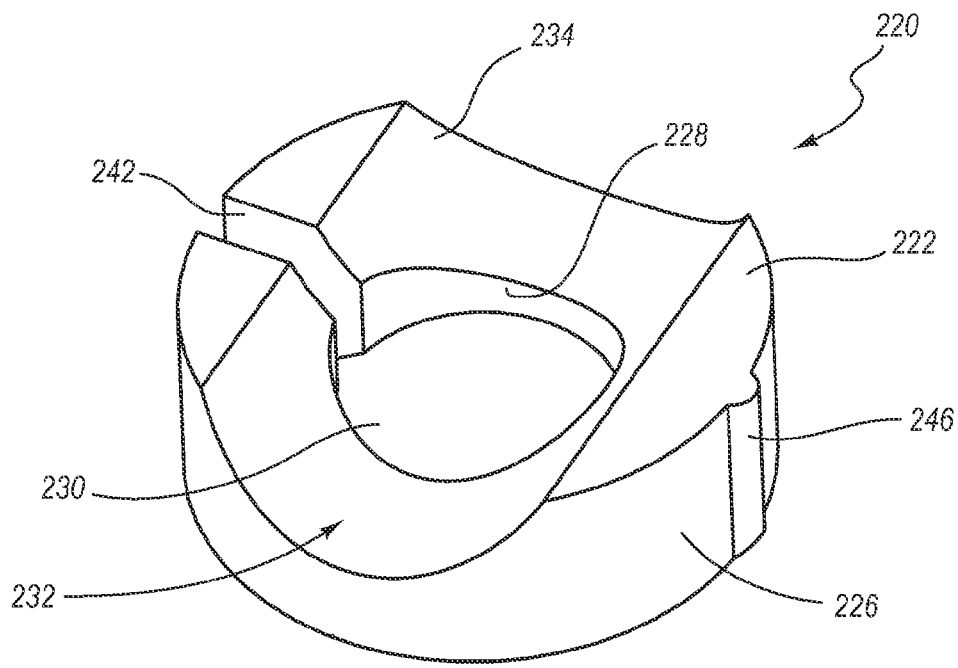
FIGS. 5A and 5B are perspective views of the saddle shown in FIG. 4.
Figure 5B:
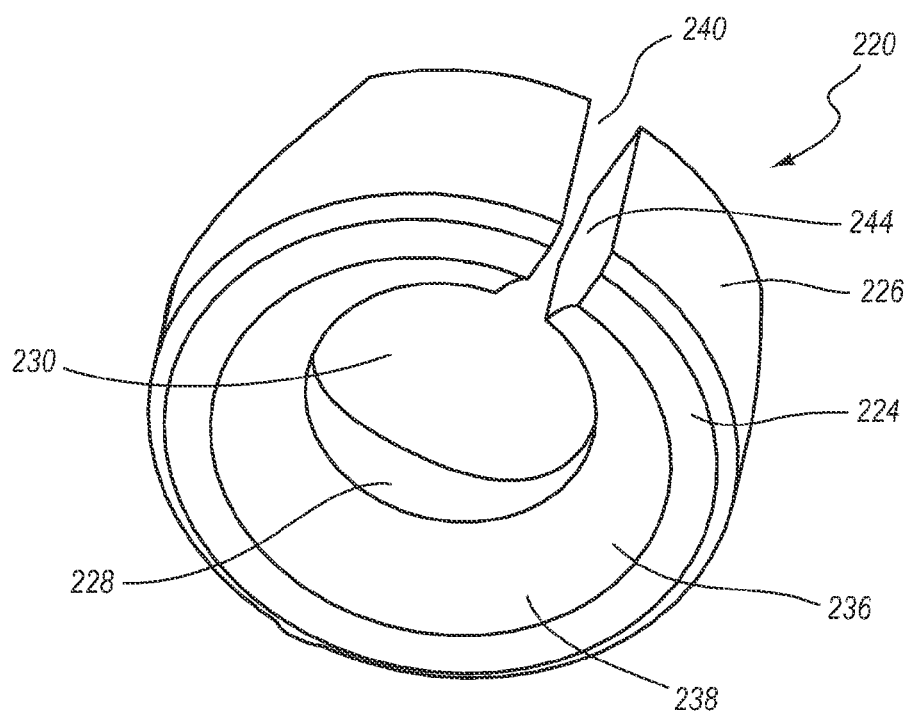

Turning to FIGS. 5A and 5B, saddle 220 has a top surface 222 and an opposing bottom surface 224 with an encircling outer side wall 226 extending therebetween. An internal side wall 228 also extends between top and bottom surfaces 222 and 224 so as to bound a central opening 230 that extends all the way through saddle 220. Opening 230 is generally circular and is sized so as to allow a driver tool to access the socket 121 on the head 119 of shaft 118 when saddle 220 is disposed against head 119. The opening 230 causes saddle 220 to be generally ring shaped when viewed from a direction generally normal to the top and bottom surfaces 222 and 224.

A substantially U-shaped channel 232 is formed on top surface 222 that extends transversally through saddle 220 so as to intersect the opening 230. Channel 232 is bounded by a curved side surface 234 sized so as to snugly receive stabilizing rod 104. As discussed in more detail below, when locking screw 200 is screwed into collar 216 (see FIG. 4), surface 234 of the U-shaped channel 232 presses against stabilizing rod 104. Although depicted as being substantially smooth, the channel surface 234 can be textured for improved gripping. Examples of the types of texture that can be used on channel surface 234 include: ribs, grooves, a waffle pattern, and an abrasive pattern. Other types of textures can also be used. See, e.g., the waffle-like texture shown in FIG. 8.

A generally concave cavity 236 is formed on bottom surface 224 so as to encircle opening 230. Cavity 236 is bounded by a curved side surface 238 sized so as to snugly receive head 119 of shaft 118 (see FIG. 2). As such, when locking screw 200 is screwed into collar 216, side surface 238 presses against head 119. As noted above, however, opening 230 in saddle 220 still allows access to socket 121 of head 119 when saddle 220 presses against head 119.

Saddle 220 has an outside diameter that is generally the same as the inner diameter of longitudinal passage 132 extending through collar 216. In some embodiments, a slit is formed in saddle 220 to allow saddle 220 to be able to be flexed for insertion into collar 216. For example, as shown in the depicted embodiment, a slit 240 is formed in saddle 220 that extends all the way between top and bottom surfaces 222 and 224 and between outer and internal side walls 226 and 228.

Slit 240 is bounded by side surfaces 242 and 244 that face each other across the slit 240. The slit 240 causes the saddle 220 to be generally "c" shaped, with the slit 240 being the mouth of the "c." As a result of the slit 240, the portions of saddle 220 on either side of slit 240 can be flexed toward each other, causing the diameter of saddle 220 to slightly decrease, thereby allowing saddle 220 to be inserted into longitudinal passage 132 of collar 216, past lip 218 during assembly (see FIG. 4). Once positioned therein, the saddle 220 resiliently springs back to its original diameter and is retained within the passage 132 by the lip 218, which has a diameter that is slightly less than that of saddle 220.

To help keep saddle 220 oriented in a desired position within collar 216, a key 246 is also positioned thereon. Key 246 comprises a spline projecting out from outer side wall 226 and extending generally orthogonally between top and bottom surfaces 222 and 224. In the depicted embodiment, key 246 is positioned on the opposite side of saddle 220 as slit 240, although this is not required; key 246 can be positioned anywhere along the outer side wall 226. As noted above, key 246 is designed to fit within corresponding channel 248 formed on interior surface 124 of collar 120 (see FIG. 4). Other types of keys can alternatively be used, or, if desired, saddle 220 can be formed without a key. In some alternative embodiments the key 246 outwardly projects from the interior surface 124 of collar 120 and the corresponding channel 248 is formed on the outer side wall 226 of saddle 220. Saddle 220 can be comprised of titanium, stainless steel, or other high strength, biocompatible metals or other materials.

Figure 6:
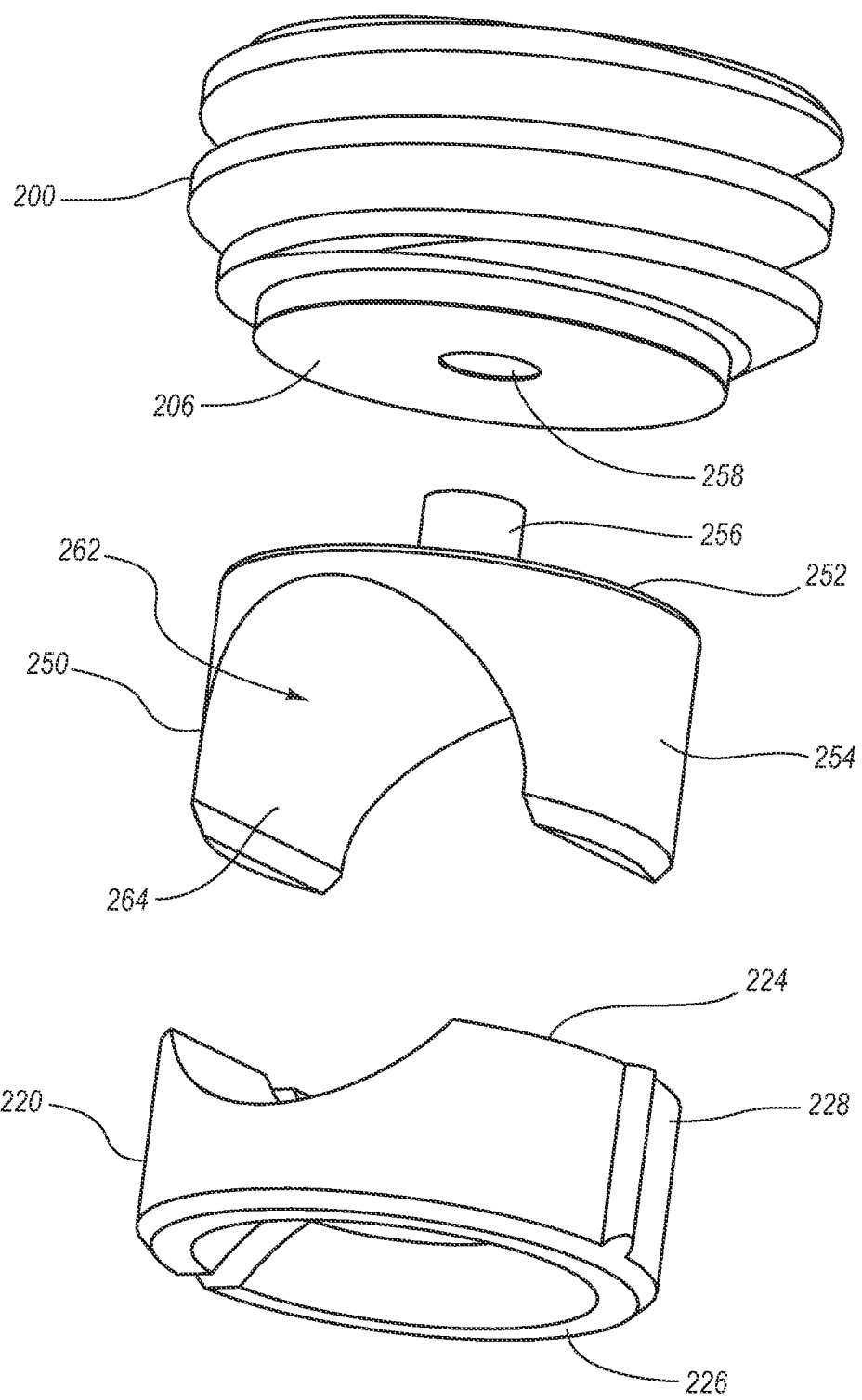
FIG. 6 is an exploded perspective view of the fastener and saddle shown in FIG. 4.

Returning to FIG. 4, fastener 112 can also include an alignment cap 250 movably attached to bottom end face 206 of locking screw 200 to further distribute the clamping forces around stabilizing rod 104. More specifically, as shown in FIG. 6, alignment cap 250 has a generally planar, circular top surface 252 with an encircling perimeter sidewall 254 extending downward therefrom. A post 256 extends upward from the center of top surface 252. Post 256 is designed to fit within a corresponding hole 258 on bottom end face 206 of locking screw 200. Alternatively, post 256 can be positioned on locking screw 200 and hole 258 can be formed on alignment cap 250

Similar to saddle 220, alignment cap 250 has a substantially U-shaped channel 262 extending transversally therethrough. Channel 262 is bounded by a curved side surface 264 sized so as to snugly receive stabilizing rod 104. Alignment cap 250 is rotatably attached to locking screw 200 by inserting post 256 into hole 258 so that as locking screw 200 is rotated, alignment cap 250 can remain rotationally stationary so as to press against stabilizing rod 104. Once inserted through hole 258, the end of post 256 can be splayed or otherwise spread apart so as to prevent the post 256 from being pulled back through hole 258, while still allowing locking screw 200 to rotate with respect to alignment cap 250. When locking screw 200 is screwed into collar 216, surface 264 of the U-shaped channel 262 presses against stabilizing rod 104. Similar to channel surface 234 of saddle 220, the channel surface 264 of alignment cap 250 can be substantially smooth or textured for improved gripping. Examples of some of the types of textures that can be used on channel surface 264 are as listed above regarding saddle 220.

Alignment cap 250 can be comprised of the same type of materials discussed above regarding saddle 220. Furthermore, alignment cap 250 can be comprised of the same material as saddle 220 or a different material.

Figure 7:
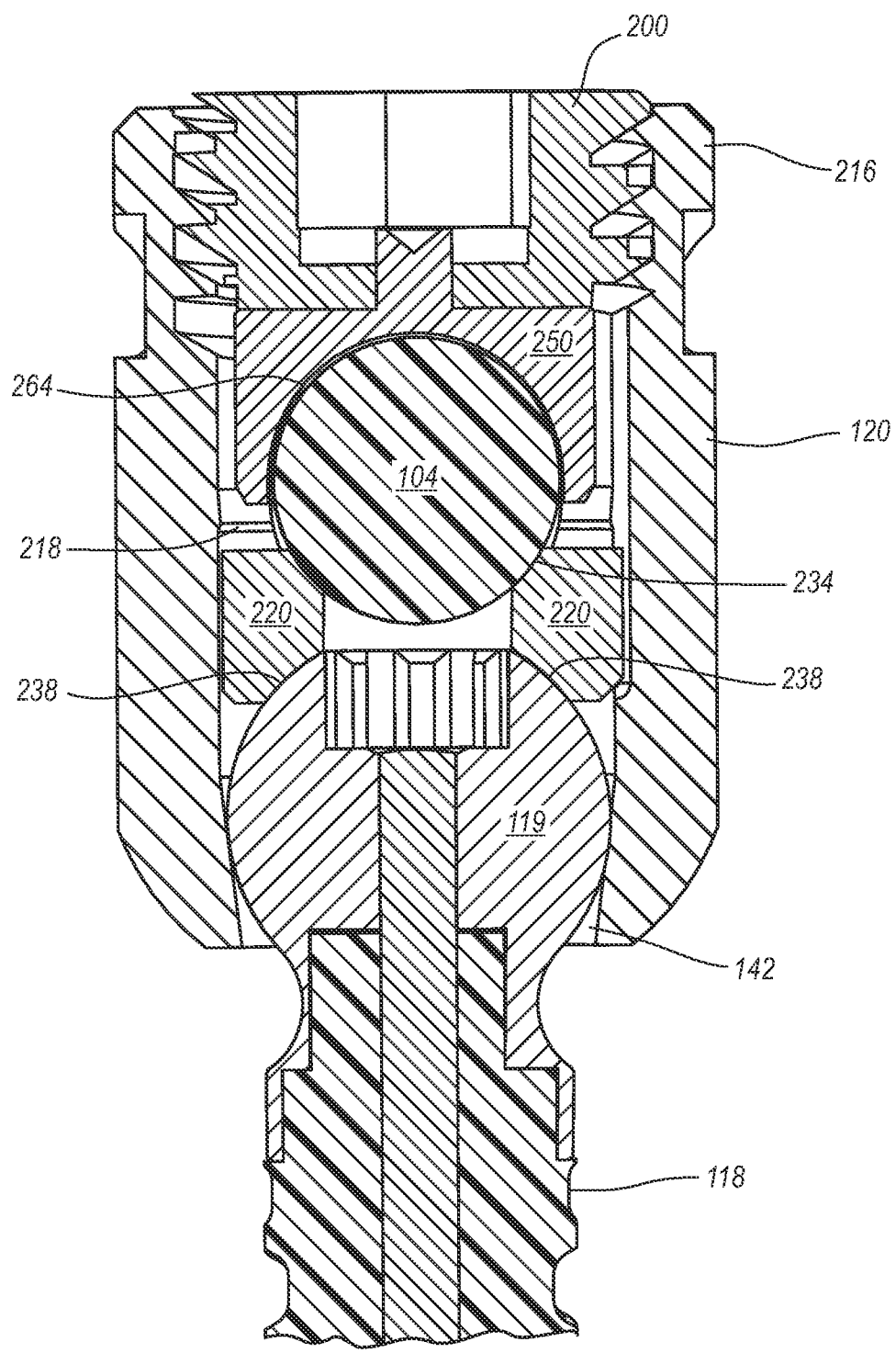
FIG. 7 is a cross-sectional side view of the assembled bone screw shown in FIG. 4, with the stabilizing rod being secured therein.

FIG. 7 shows how the saddle 220 and alignment cap 250 combine to secure stabilizing rod 104 within collar 216. As discussed above, when locking screw 200 is screwed into collar 216 while stabilizing rod is disposed within channels 136 and 138, surface 264 of alignment cap 250 presses against stabilizing rod 104. This pressure causes stabilizing rod 104 to, in turn, press against surface 234 of saddle 220, which causes surface 238 of saddle 220 to press against head 119 of shaft 118. As a result, stabilizing rod 104 is rigidly attached to bone screw 108 while the clamping forces are distributed around stabilizing rod 104 by saddle 220 and alignment cap 250.

As can be appreciated, saddle 220 and alignment cap 250 can be used together, as shown in FIG. 7, or separately. That is, saddle 220 and alignment cap 250 are not reliant on each other and thus can be used with or without the other, as desired. Furthermore, the surfaces 234, 254, and 256 of channels 232 and 248 can be textured the same or have different textures from each other. Alternatively, a texture may be used on only one or more of the surfaces or, of course, all of the surfaces can be free of any texturing.

Figure 8:
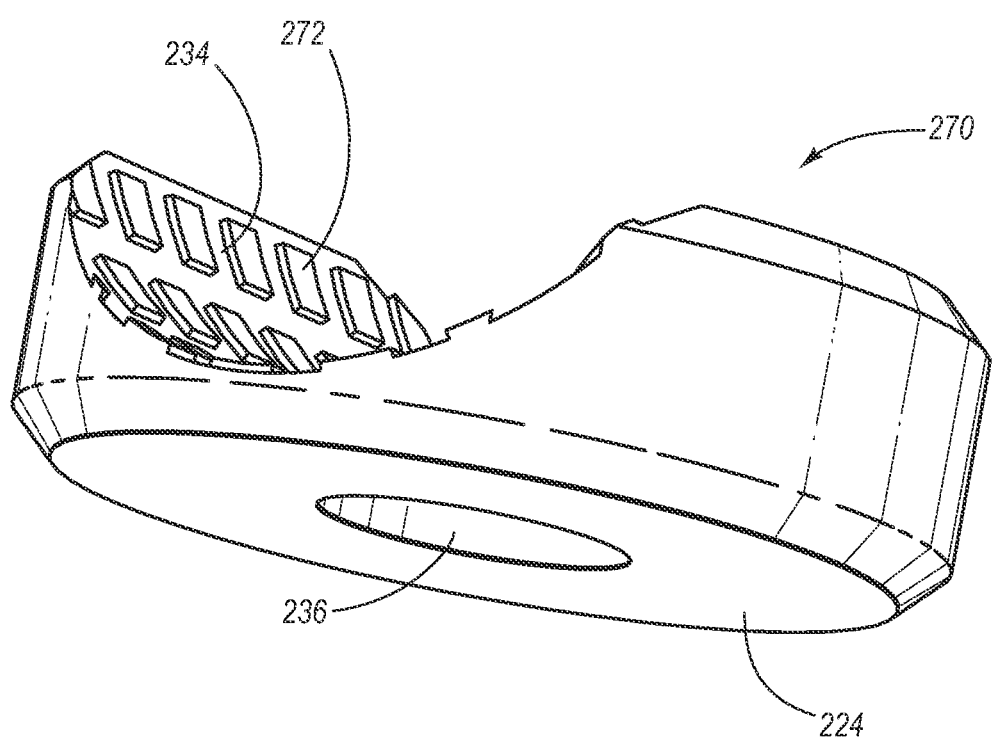
FIG. 8 is a perspective view of another embodiment of a saddle.

FIG. 8 shows an alternative embodiment of a saddle 270 that can be used in the current invention. Saddle 270 is similar to saddle 220, except that there is no opening or slit extending through the saddle. Instead, a closed end cavity 236 is formed on bottom surface 224 that is configured to receive head 119 (FIG. 7). Saddle 270 also includes a waffle-like texture 272 on side surface 234. Of course, as discussed above, other types of textures can also be used.

As can be appreciated, bone screw 116 and corresponding fastener 112, with or without saddle 220, are but one example of a bone screw/fastener combination that can be used with the present invention. Other bone screws and fasteners as are known in the art can also be used. In some embodiments collets or other spacers can be included in the bone screw.

A number of examples of other bone screws and fasteners that can be used with the present invention are disclosed in U.S. Patent Publication Nos. 2008/0243185 A1, published Oct. 2, 2008 and 2010/0063550 A1, published Mar. 11, 2010, which are incorporated herein by specific reference. Although bone screws of the present invention are typically comprised of titanium or other high strength, medical grade metals, the bone screws can also be comprised of a radiolucent material having a radiopaque marker as disclosed in above referenced Publication No. 2010/0063550 A1. It is appreciated that other conventional bone screws known in the art can also be used in the present invention.

Returning to FIG. 2, in one embodiment stabilizing rod 104 has a substantially cylindrical configuration and, as noted above, is sized to fit within transverse passage 140 of collar 120. In the depicted embodiment, stabilizing rod 104 is substantially straight. However, this is not necessary. In other embodiments, stabilizing rod can be curved or can comprise a combination of straight and curved sections.

Figure 9:
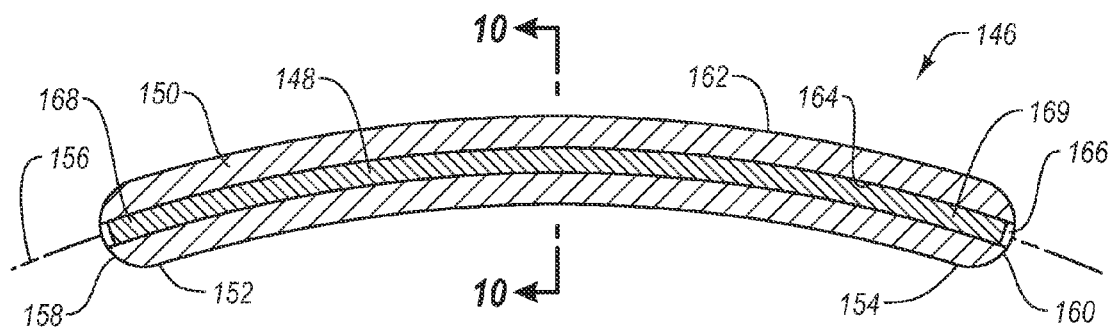
FIG. 9 is a cross-sectional side view of a curved stabilizing rod according to one embodiment.
Figure 10:
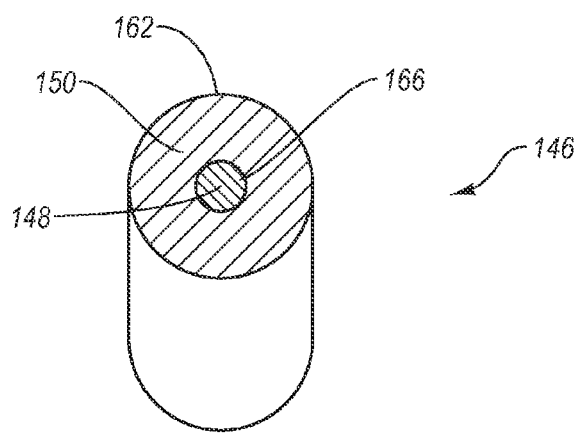
FIG. 10 is a cross-sectional view of the stabilizing rod shown in FIG. 8, taken along the section line 10-10 in FIG. 9.

For example, FIGS. 9 and 10 show one embodiment of a stabilizing rod 146 curved in a continuous arc according to the present invention. Whether straight or curved, stabilizing rods 104, 146 typically have a substantially circular transverse cross section. However, in alternative embodiments the stabilizing rod need not have a circular cross section but can have an elliptical, polygonal, irregular or other cross sectional configuration. However, having a circular transverse cross section provides for uniform engagement and seating with bone screws 108, 110, fastener 112, and cross link 102. Stabilizing rods 104, 146 typically have a maximum outside diameter in a range between about 3 mm to about 12 mm with about 4 mm to about 8 mm being more common. Other diameters can also be used.

Continuing with FIGS. 9 and 10, stabilizing rod 146 comprises an elongated tubular shaft 150 with a core 148 extending longitudinally therethrough. Shaft 150 extends along a central longitudinal axis 156 between a proximal end 152 and a spaced apart distal end 154. Central longitudinal axis 156 is either straight or curved to match the contour of shaft 150. A proximal end face 158 and a distal end face 160 are respectively disposed at proximal end 152 and distal end 154 of stabilizing rod 146.

It is appreciated that the inventive stabilizing rods can come in a variety of different lengths depending on the intended use of the stabilizing rod. For example, stabilizing rods according to the present invention will be considerably longer if intended for use in a system for stabilizing multiple sequential vertebrae in a spine as opposed to stabilizing only two adjacent vertebrae in a spine. The stabilizing rods of the present invention typically have a length extending between end faces 158 and 160 in a range between about 25 mm to about 460 mm, with about 30 mm to about 300 mm being common and about 30 mm to about 100 mm being common. Other lengths are also possible. The inventive stabilizing rods can also be formed in a number of different standard lengths such as 45 mm, 55 mm, 65 mm, 75 mm, and 85 mm each at ±5 mm.

In the depicted embodiment, longitudinal axis 156 is curved and shaft 150 is correspondingly curved. In other embodiments, such as in FIG. 2, longitudinal axis 156 is substantially linear and shaft 150 is correspondingly substantially straight. In still other embodiments the shaft and longitudinal axis can comprise a combination of straight and curved sections. The curvature is again dependent on the intended use.

Shaft 150 has an exterior surface 162 that extends between proximal end face 158 and distal end face 160. Shaft 150 also includes an internal surface 164 that bounds a passageway 166 extending through shaft 150 between proximal end 152 and distal end 154. Passageway 166 extends along longitudinal axis 156 and may or may not extend through one or both end faces 160 and 162. In the embodiment depicted, passageway 166 has a substantially circular cross-sectional shape. Other shapes can alternatively be used for passageway 166. For example, passageway 166 can be oval shaped, star shaped, polygonal shaped, irregular or the like. Passageway 166 can also be symmetrically or non-symmetrically shaped.

Shaft 150 can be comprised of a radiolucent material that will allow viewing of adjacent bone or other internal structures on an X-ray photograph that are in the viewing path of shaft 150. Using radiolucent material for the shaft 150 will also minimize scattering caused by commonly used metals in X-Rays, CAT scans, MRI's, and other types of imaging systems.

One example of a radiolucent material that can be used in shaft 150 is a radiolucent biocompatible fiber and adhesive matrix. In this embodiment, an adhesive is applied to one or more elongated biocompatible fibers that are then wound about core 148 or some other structure to form shaft 150. This is typically done by winding two or more layers of fibers about core 148. The fibers can be wound one fiber at a time or multiple fibers at a time in a fiber bundle or tow. The fibers are typically of indefinite length and are wound from a spool or other carrier and then cut when the winding is completed. Alternatively, the fibers can comprise one or more shorter fibers that are wound about core 148 or chopped fibers that are dispersed in the adhesive. In still other embodiments, the fibers can be included in a sheet and the sheet wound about core 148 in one or two or more layers. Various winding patterns can also be used. Methods of manufacturing the shaft 150 and other portions of the stabilizing rod 146 are discussed in more detail below.

Many different types of biocompatible fibers and adhesives can be used to form radiolucent shaft 150. For example, the fibers can be comprised of carbon, fiberglass, poly paraphenylene terephthalamide (PPTA, more commonly known as Kevlar®), other aramids, and ceramics. Other radiolucent, biocompatible fibers having desired properties can also be used.

Although fibers having multiple different properties can be used, typical fibers have a diameter in a range between about 5 microns to about 18 microns with about 5 microns to about 7 microns being more common and a tensile strength in a range between about 300 ksi to about 1000 ksi with about 600 ksi to about 1000 ksi being more common. Other diameters and tensile strengths can be used. The fibers can be sized or unsized. By "unsized," it is meant that the fibers have not been coated with a material to improve adhesion of the resin or adhesive. If the fibers are sized, biocompatibility of the sizing needs to be considered. When bundles of fibers are used, the tow of the fibers (i.e., the number of fibers per bundle) can range from about 1 k to about 72 k with about 3 k to about 24 k being more common.

Other tow ranges can also be used. In one specific embodiment, the fibers comprise a continuous high strength, PAN based carbon fiber, 34-700, 12 k (tow), "unsized". In another specific embodiment, the fibers comprise a continuous high strength, PAN based carbon fiber, 34-700, 3 k (tow), sized.

Examples of biocompatible adhesives that can be used with the fibers include thermoplastic materials, thermoset materials and ceramics. Examples of thermoplastic materials that can be used include polyester, vinylester, polycarbonate, polyetheretherketone (PEEK), polyaryletherketone (PAEK), polyethylene, polyurethane, and polyamide. Examples of thermoset materials that can be used include epoxies and polyimides. Exemplary biocompatible epoxies include the Master Bond Inc. epoxies EP42HT-2 and EP45HT MED and the Epotek epoxies 301-2 and 375. Examples of ceramics that can be used include alumina and zirconia. Other epoxies, ceramics, plastics and/or resins that are implantable, biocompatible, sterilizable, and have the desired strength properties can also be used. In an alternative embodiment, the radiolucent material used in shaft 150 can simply comprise the adhesive materials as discussed above without the fibers. If desired, other additives and fillers can be combined with the adhesive materials.

Continuing with FIGS. 9 and 10, core 148 comprises a slender rod that extends between a proximal end 168 and an opposing distal end 170. Core 148 is designed to be disposed within passageway 166 of shaft 150 of stabilizing rod 146. As discussed below, this can be accomplished by forming shaft 150 about core 148 or by inserting core 148 into passageway 166 after the passageway has been formed. As such, core 148 can be curved, linear, or a combination thereof to match the longitudinal configuration of passageway 166. For example, in the depicted embodiment, core 148 is curved in a continuous arc between proximal end 152 and distal end 154, whereas in stabilizing rod 104 (FIG. 2), core 148 (not shown) is substantially linear. Furthermore, core 148 can have the same cross sectional shape as passageway 166. For example, in the embodiment depicted, core 148 has a substantially circular cross section to match the circularly shaped passageway 166.

Figure 11A:
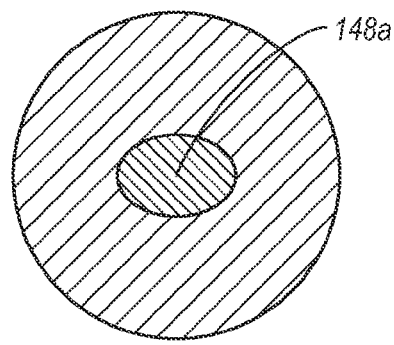
FIGS. 11A-11D are cross-sectional views of alternative embodiments of stabilizing rods.
Figure 11B:
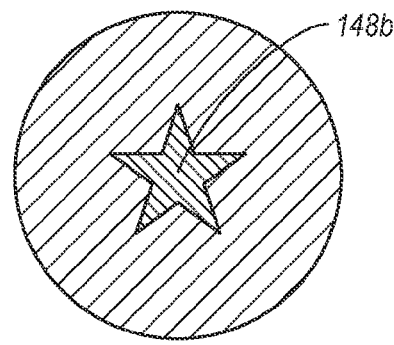
Figure 11C:
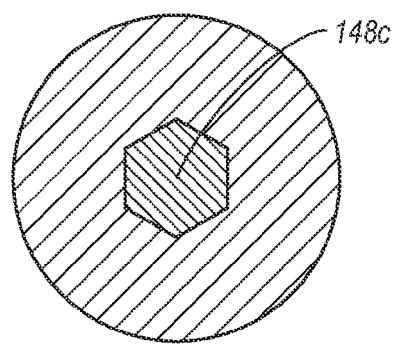
Figure 11D:
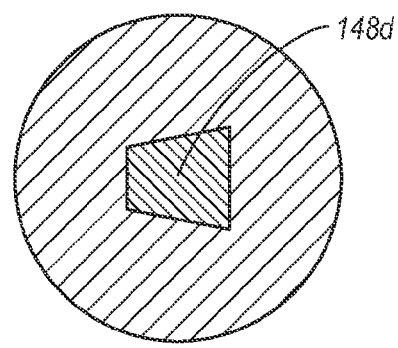
Figure 11E:
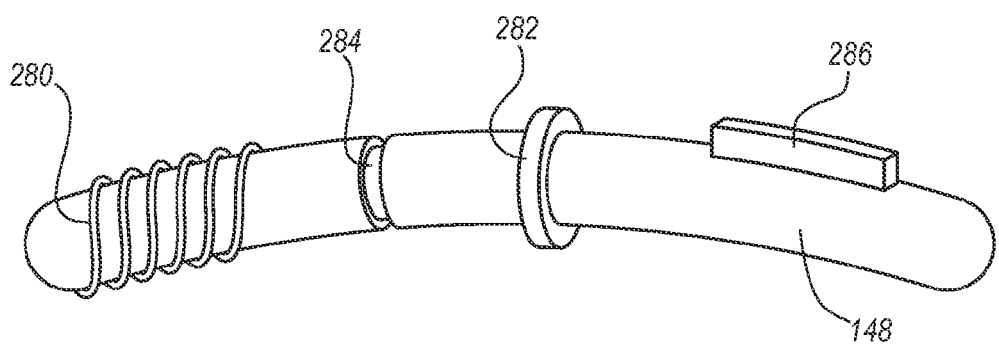
FIG. 11E is a side view of an alternative embodiment of a core of a stabilizing rod.

Various geometric cross sectional shapes can alternatively be used for core 148. For example, FIGS. 11A-11D disclose various embodiments of core 148 having different cross sectional shapes. FIG. 1A shows an embodiment in which core 148a is oval shaped. FIG. 1B shows an embodiment in which core 148b is generally star shaped. FIG. 11C shows an embodiment in which core 148c is generally polygonal shaped. In some embodiments core 148 has a symmetrical cross sectional shape, such as core 148c shown in FIG. 11C; in other embodiments core 148 has a non-symmetrical cross sectional shape, such as core 148d shown in FIG. 11D. It is appreciated that the aforementioned core shapes are exemplary only and that other shapes can alternatively be used. By way example and not by limitation, FIG. 11E shows core 148 having a helical thread 280 formed on the exterior surface of core 148. Helical thread 280 can extend along a portion of or the entire length of core 148. Core 148 can also be formed with one or more annular flanges 282, annular recesses 284, and/or ribs 286 outwardly projecting from or being recessed on the exterior surface of core 148. Other recesses and/or projections can be formed on core 148 to further help the engagement between core 148 and shaft 150.

It is appreciated that the passageway 166 in shaft 150 in which core 148 is received can have the same complementary configuration as core 148 or can be different. One benefit of producing core 148 with a non-circular configuration is that greater engagement can be formed between core 148 and shaft 150 of stabilizing rod 146, thereby minimizing the potential for separation therebetween.

Core 148 typically has a maximum outer diameter in a range between about 1 mm to about 3.5 mm, with about 2 mm to about 3 mm being common. In one embodiment, core 148 has a maximum diameter that is less than about 3 millimeters and more commonly less than about 2 millimeters. Other diameters can also be used. By having core 148 with a rather small diameter, core 148 minimize obstruction of adjacent bone and other structures during imaging and likewise minimizes scattering and distortion caused by metals during imaging. Nevertheless, core 148 still provides a very clear marking for determining the position of the stabilizing rod by using conventional imaging techniques.

Core 148 is typically comprised of a radiopaque material, such as certain metals. Examples of radiopaque metals that can be used in core 148 are titanium, stainless steel, tungsten, cobalt based alloys, cobalt chrome alloys, nickel titanium alloys such as Nitinol, platinum/iridium, gold, barium and alloys thereof. Other radiopaque materials that can be used include cortical bone and synthetic bone. The radiopaque material may also comprise the radiolucent materials discussed above having a radiopaque filler disposed therein. Other radiopaque, biocompatible metals or other materials can also be used. One advantage of using a radiopaque material in core 148 while using a radiolucent material in shaft 150 is that only the thin core 148 will be seen on an X-ray during and after implantation of stabilizing rod 146. This aids the surgeon by conveying a precise position of stabilizing rod 146 during and/or after implanting stabilizing rod 146 while simultaneously minimizing the obstruction of surrounding bones and other structures. Where core 148 is comprised of a radiopaque material, core 148 comprises a marker for the stabilizing rod.

Applicant notes that due to the electric potential between carbon and titanium, corrosion may occur between the two surfaces in the presence of an electrolyte. However, because the electron potential is small, the corrosion would be very small, if it occurs at all. Furthermore, the adhesive used in the matrix acts as an insulator. To combat any corrosion that may occur, anodization or passivation of the metals can be performed before assembly.

In alternative embodiments, core 148 can be comprised of a radiolucent material, such as those materials previously discussed with regard to shaft 150. For example, core 148 can comprise an adhesive as discussed with regard to shaft 150 that is free of fibers or that that has elongated or chopped fibers embedded therein. Alternatively, core 148 can be comprised of a ceramic or thermoplastic material while shaft 150 is comprised of a thermoset material with fibers. In these embodiments, the stabilizing rod can be completely free of any radiopaque markers or, alternatively, one or more radiopaque markers can be added thereto, as discussed below. In still other embodiments, core 148 can be comprised of both radiolucent and radiopaque materials. For example, small pieces of radiopaque material, such as small pieces of metal can be embedded within or spaced between a matrix of a radiolucent material such as an epoxy.

In one method of manufacture, the radiolucent fibers and adhesive can be wound around a removable rod. Once shaft 150 is formed by the radiolucent material about the rod, the rod is removed leaving passageway 166. Passageway 166 can then be backfilled with a radiolucent material as discussed above or a combination of radiolucent and radiopaque materials. As a result, if desired, radiopaque material can be positioned at a defined location or at select, spaced apart locations along passageway 166 to form one or more defined markers under X-ray.

Based on the foregoing, it is appreciated that inventive stabilizing rod can be comprised of a radiolucent shaft 150 with a radiopaque core 148; a radiolucent shaft 150 with a radiolucent core 148; and/or a radiolucent shaft 150 with a core 148 having both radiolucent and radiopaque sections. In combination with each of the above three alternative designs, it is appreciated that radiopaque markers can be formed on or along the radiolucent shafts 150. Such markers can further aid in the implantation and positioning of the stabilizing rod.

Figure 12:
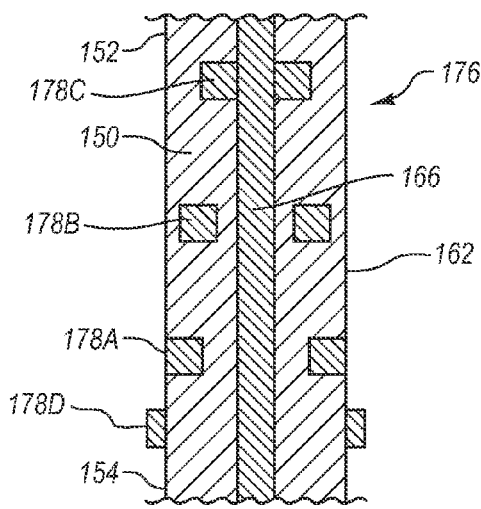
FIG. 12 is a cross sectional side view of a portion of a stabilizing rod according to one embodiment having a ring positioned therein.

One example of a radiopaque marker is an encircling marker disposed within or on shaft 150 such that the marker is spaced apart or is disposed directly against core 148. For example, FIG. 12 shows an embodiment of a stabilizing rod 176 in which a biocompatible positioning marker 178A is embedded within shaft 150 between proximal end 152 and distal end 154. In the depicted embodiment, positioning marker 178A can comprise a ring that completely encircles passageway 166 or a partial ring that partially encircles passageway 166. In other embodiments, positioning marker 178A can be linear or any other desired shape. Each positioning marker 178A can be positioned so as to be exposed on the exterior surface of shaft 150 (such as positioning marker 178A), completely embedded within shaft 150 (such as positioning marker 178B), positioned against core 148 (such as positioning marker 178C), or can extend between core 148 and the exterior surface of shaft 150. Furthermore, a positioning marker 178D, such as in the form of a ring or other structure, can be disposed on the exterior surface 162 of shaft 150. This can be accomplished by welding, crimping, adhering, or otherwise securing positioning marker 178D on exterior surface 162. Other configurations and placement of positioning markers 178 can also be used. For example, a positioning marker can form a helix that spirals in one or more partial or complete revolutions about passageway 166 or can form a linear strand that extends along the length of shaft 150.

Positioning markers 178 are comprised of a radiopaque material so as to be viewable on an X-ray photograph. As such, positioning markers 178 can be comprised of the same types of radiopaque materials discussed above with regard to core 148. During implantation and positioning of stabilizing rod 146, the X-ray image of positioning markers 178 can help the physician determine the position and orientation of stabilizing rod 146.

In one embodiment, a positioning marker 178 is positioned about midway between proximal end 152 and distal end 154 of shaft 150. In other embodiments, a positioning marker 178 is positioned substantially closer to proximal end or distal end 154 or at any desired location. In other embodiments, as shown in FIG. 12, it is appreciated that two or more positioning markers 178 can be positioned along shaft 150 at spaced apart locations.

Figure 13:
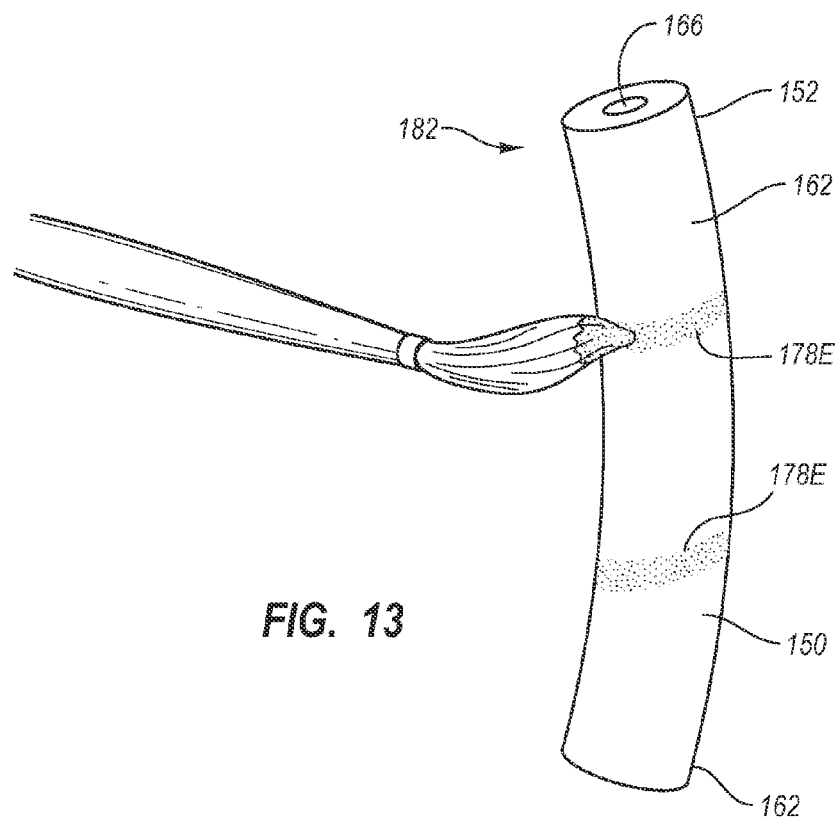
FIG. 13 is a perspective view of a stabilizing rod according to one embodiment having a ring layer painted thereon.

Depicted in FIG. 13 is another embodiment of a positioning marker 178E. Positioning marker 178E is again comprised of a radiopaque material but in this embodiment is in the form of paint or ink that is painted or printed onto exterior surface 162 of shaft 150. Positioning marker 178E can be used in place of or in combination with one or more additional positioning markers as discussed above. Positioning marker 178E can form a continuous ring that encircles shaft 150 or can be any other type of configuration such as linear, semi-circular, helical configuration or the like. Furthermore, a single or two or more spaced apart positioning markers 178E can be formed along shaft 150.

It is appreciated that radiopaque markers can be any desired shape and be located at any position or orientation that will produce a desired marking. For example, returning to FIG. 2, an end cap 186, which comprises a radiopaque positioning marker, is positioned at proximal end 152 of stabilizing rod 104. It is appreciated that end cap 186 can also be placed on distal end 154 of stabilizing rod 104 in conjunction with or in place of end cap 186 at proximal end 152. In the depicted embodiment, end cap 186 is substantially disc shaped and has substantially the same diameter as shaft 150 so as to cover all of proximal end face 158.

Other configurations are also possible. For example, in other embodiments, end cap 186 can be I-shaped, or X-shaped, or some other non-circular configuration so as to only partially cover proximal end face 158. In still other embodiments, end cap 186 can have a diameter that is less than the diameter of shaft 150 or can have a non-disc shape. Similar to the positioning markers 178, end cap 186 is comprised of a radiopaque material so as to be viewable on an X-Ray photograph. As such, end cap 186 can be comprised of the same types of radiopaque materials discussed above with regard to core 148. It is appreciated that stabilizing rods having any combination of radiopaque positioning markers is envisioned by the present invention.

In other embodiments, pieces of radiopaque material can be embedded within the shaft matrix as radiopaque positioning markers. These pieces can comprise small or large particles that are placed within the shaft matrix during manufacture either randomly or in a particular pattern. Many different shapes and patterns can be used for these radiopaque positioning markers. Also, these pieces of radiopaque material can be used with or without any of the other types of positioning markers discussed above.

Methods of manufacturing and assembling the stabilizing rod 146 will now be discussed. It is appreciated that while reference is made to stabilizing rod 146 and its corresponding components, the methods of manufacturing and assembly given below can also be used with many, if not all, of the other embodiments disclosed herein or otherwise encompassed by the invention. To manufacture stabilizing rod 146, core 148 is formed from a radiopaque material, a radiolucent material, or a combination of such materials. Examples of such materials are discussed above. Core 148 can be formed by any conventional method known in the art.

Shaft 150 is then formed about core 148 to produce a blank 190, as shown in FIGS. 14-16. Blank 190 can be formed in a number of ways. For example, blank 190 can be formed by winding a fiber and adhesive mixture about core 148 to produce a fiber and adhesive matrix. For example, in the embodiment depicted in FIG. 14, a filament winding process is used as is known in the art. In this process, filaments or fibers 192 are wound under tension over core 148. Core 148 rotates while a carriage (not shown) moves back and forth along the longitudinal direction of core 148, laying down fibers 192 in a desired pattern. Fibers 192 are coated with an adhesive as the fibers 192 are wound about core 148. Many types of biocompatible fibers and adhesives can be used, as discussed above.

If a positioning marker 178 (such as marker 178A-C in FIG. 12) is used, the positioning marker 178 can be positioned in its desired location during the filament winding process so that the positioning marker 178 becomes enveloped by the outer layers of fibers 192. The marker can also be positioned before or after the winding process. The winding process continues until the diameter of the blank 190 is equal to or greater than the desired diameter of the finished shaft 150 of stabilizing rod 146. Blank 190 is then allowed to cure or harden. If required, blank 190 can be placed in an oven during the curing process.

In an alternative embodiment, blank 190 is formed using a roll wrap or table wrap process, as depicted in FIG. 15. In this process, one or more sheets 194 of fiber are coated with the adhesive. Many types of biocompatible fibers and adhesives can be used, as discussed above. If required, the coated sheet or sheets 194 are then allowed to partially cure. Once the desired amount of partial curing has been obtained, the sheet or sheets 194 are then wrapped about core 148 to produce a fiber and adhesive matrix. Again, if a positioning marker 178 (FIG. 12) is used, it can be positioned in its desired location during the wrapping process so that positioning ring 178 becomes enveloped by the outer layers of sheets 194. That is, multiple different layers can be wrapped on top of each other. The marker can also be positioned before or after the wrapping. The wrapping continues until the diameter of the blank 190 is greater than or equal to the desired diameter of the finished shaft 150 of stabilizing rod 146. Blank 190 is then allowed to cure in a similar manner to the filament winding process, described previously.

It is also appreciated that non-winding methods can also be used for forming blank 190 about core 148. For example, compression, injection, rotational and other molding processes can be used to mold a fiber/adhesive mixture about core 148. In this embodiment, the fibers can be short or chopped fiber pieces that are distributed throughout the adhesive. As another alternative, stabilizing rod 146 can be formed by a direct or indirect extrusion process, where the fiber/adhesive matrix is extruded about core 148. Other known methods can alternatively be used to form blank 190.

To allow for a better bond between core 148 and the fiber and adhesive matrix, the surface of core 148 can be etched or otherwise abraded before the fibers 192 or sheets 194 are wound or otherwise formed thereabout. This can be accomplished by sand blasting, rubbing with sandpaper, chemical etching, or other known roughening process, if desired.

Once the blank 190 has been formed and allowed to cure, a grinder or other finishing process can be used, if desired, to smooth or cut down the exterior surface 196 of the blank 190 to form the exterior surface 162 of the shaft 150. If positioning marker 178D or 178E is used (FIGS. 12 and 13), it is positioned or painted on the exterior surface 162 of shaft 150 after blank 190 has been processed. Furthermore, if one or more end caps 186 (FIG. 2) are used, the end caps 186 can be attached by adhesive or welding or other manner known in the art to either of the end faces 158 are 160 after the blank 190 has been formed.

In an alternative method of manufacturing stabilizing rod 146, shaft 150 can initially be formed by winding a radiolucent fiber/adhesive matrix about a core 148 that is formed from a high strength radiopaque material, such as a metal. In contrast to prior embodiments, however, core 148 is then slid out of shaft 150. The remaining passageway can then be backfilled by injecting a radiolucent material, such as an epoxy or other adhesive, or a combined radiolucent and radiopaque material into the passageway. Alternatively, a radiolucent core can be slid into the passageway and secured in place by an adhesive or other method of securing. As a result, the entire shaft and core are radiolucent. Again, any number or type of radiopaque positioning marker can be used.

Depicted in FIG. 17 is an exploded perspective view alternative embodiments of a stabilizing rod 300 incorporating features of the present invention wherein like elements are identified by like reference characters. Stabilizing rod 300 includes shaft 150 having passageway 166 extending therethrough. Having, in contrast to having core 148 disposed within shaft 150, stabilizing rod 300 can be formed with one of several different cores.

In one embodiment a core 302 is used which comprises an elongated solid, inner core 304. Inner core 304 can have substantially the same configuration as core 148 previously discussed but may have a smaller diameter. Inner core can be made of a radiolucent material or radiopaque material as discussed herein. Core 302 also includes a tubular outer core 306 that extends over at least a portion of inner core 304. Outer core 306 is comprised of a radiopaque metal wire or ribbon that is coiled into the tubular configuration so as to bound a passageway 308 longitudinally extending therethrough. The material for outer core 306 is selected so that outer core 306 is resiliently flexible like a coiled spring. For example, in one embodiment the wire or ribbon of outer core 306 is comprised of Nitinol and is heat treated when in the coiled configuration so that it obtains a coiled memory. Other metals can also be used. The wire or ribbon can be coiled directly around inner core 304 or can be separately coiled and then placed over inner core 304.

Outer cores 306 can be secured to inner core 304 by an epoxy, other adhesives or by other fastening techniques. Outer core 306 can cover all or substantially all of inner core 304. Alternatively, outer core 306 can be sized to cover only a portion inner core 304. To that end, the outer core 306 can cover not more than 65% and commonly not more than 75% of the length of inner core 304. Shaft 150 is formed about outer core 306 in the same manner as previously discussed.

In another alternative, shaft 150 can be formed about a core 310. Core 310 is the same as outer core 306 except that an inner core is not positioned within passageway 308 of core 310. Rather, passageway 308 can remain empty. In either of the above embodiments, by forming core 306/310 from a coiled wire or ribbon having resilient spring properties, the flexible properties of the resulting stabilizing rod 300 can be adjusted.

In yet another alternative, shaft 150 can be formed on an elongated, tubular core 312. Core 312 comprises a solid tubular sleeve that bound a passageway 314 longitudinally extending therethrough. Core 312 can be comprised of a radiolucent material or a radiopaque material such as the materials previously discussed herein. It is appreciated that passageway 314 can remain empty, a core, such as inner core 304 can be disposed therein, or a material can be back filled, such as by injection, into passageway 314.

A number of different methods and embodiments are disclosed herein. It is appreciated that the different methods and components from the different embodiments can be mixed and matched to produce a variety of still other different embodiments.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A stabilizing rod for use in positioning adjacent vertebrae with respect to each other, the stabilizing rod comprising:
    an elongate shaft extending longitudinally between a proximal end and an opposing distal end, the shaft having a first end face disposed at the proximal end, a second end face disposed at the distal end, and an encircling side surface extending between the end faces, the shaft having a central longitudinal axis extending between the proximal end and the distal end and bounding a passageway that extends along the central longitudinal axis so that the central longitudinal axis is disposed within the passageway, the shaft being comprised of a radiolucent material and the encircling side surface consisting entirely of a radiolucent material, the radiolucent material comprising a matrix of fiber and adhesive; and a solid core having an encircling exterior side surface that extends between opposing end faces, the solid core being disposed within the passageway of the shaft and extending between the proximal and distal ends of the shaft so that the core extends along the central longitudinal axis of the shaft, the solid core being comprised of a radiopaque material and being bonded to the shaft by the adhesive of the shaft along the entire length of the core, the solid core having the configuration of a rod and being the only rod that extends along the length of the shaft, wherein the matrix of fiber and adhesive is wound around the core so that the fiber encircles the core in a helical pattern, wherein the matrix of fiber and adhesive is bonded together so that at least a section of the shaft extends continuously as a unitary bonded structure between the opposing end faces of the shaft without encircling the core.

2. The stabilizing rod as recited in claim 1, wherein the rod has a diameter that is between about 3 mm to about 8 mm and the rod has a length that is between about 25 mm to about 460 mm.

3. The stabilizing rod as recited in claim 1, wherein the passageway extends longitudinally completely through the shaft.

4. The stabilizing rod as recited in claim 1, wherein the shaft is substantially straight.

5. The stabilizing rod as recited in claim 1, wherein the shaft and the core are curved in a continuous arc between the proximal end and the distal end.

6. The stabilizing rod as recited in claim 1, wherein the radiolucent material comprises a carbon fiber epoxy matrix.

7. The stabilizing rod as recited in claim 1, wherein the core has a cross-sectional shape that is polygonal, oval, non-symmetrical, or has at least one linear surface.

8. The stabilizing rod as recited in claim 1, further comprising at least one positioning marker disposed on or within the shaft, the at least one marker being comprised of a radiopaque material.

9. The stabilizing rod as recited in claim 8, wherein the at least one positioning marker is in the form of a ring that encircles the core.

10. The stabilizing rod as recited in claim 8, wherein the at least one positioning marker comprises an end cap disposed on the proximal end or distal end of the shaft.

11. The stabilizing rod as recited in claim 8, wherein the at least one positioning marker comprises a paint or ink that is painted or printed on an exterior surface of the shaft.

12. The stabilizing rod as recited in claim 1, wherein the core has an interior surface that bounds a passageway longitudinally extending through the core.

13. The stabilizing rod as recited in claim 1, wherein the core is a tubular member comprised of a metal wire or ribbon that is coiled in a helical configuration.

14. A bone stabilizing system, comprising:
a bone screw having a collar with a channel transversely extending therethrough;
a rod according to claim 1, the rod having a cross section that is configured to fit within the channel; and
a fastener configured to secure the rod to the bone screw within the channel.

15. The bone stabilizing system as recited in claim 14, wherein a portion of the rod is disposed within the channel and is secured to the bone screw by the fastener.

16. The bone stabilizing system as recited in claim 15, further comprising:
a second bone screw having a second collar with a second channel transversely extending therethrough; and
a second fastener that secures a second portion of the rod to the second bone screw within the second channel.

17. The stabilizing rod as recited in claim 1, wherein the core comprises a solid metal rod.

18. The stabilizing rod as recited in claim 17, wherein the diameter of the rod is between about 3 mm to about 8 mm and the length of the rod is between about 30 mm to about 100 mm.

19. A bone stabilizing system comprising:
a bone screw having a collar with a channel transversely extending therethrough;
a rod according to claim 17, the rod having a cross section that is configured to fit within the channel; and
a fastener configured to secure the rod to the bone screw within the channel.

20. The stabilizing rod as recited in claim 17, wherein the core is the only rod secured to the shaft.

21. The stabilizing rod as recited in claim 1, wherein the core has a central longitudinal axis extending along the length thereof, the central longitudinal axis of the core being disposed along the central longitudinal axis of the shaft.

22. The stabilizing rod as recited in claim 1, wherein the matrix of fiber and adhesive is in the form of a sheet that is wound around the core.

23. The stabilizing rod as recited in claim 1, wherein the adhesive comprises polyetheretherketone (PEEK) or polyaryletherketone (PAEK).

24. The stabilizing rod as recited in claim 1, wherein the fiber comprises a carbon fiber.

25. The stabilizing rod as recited in claim 1, wherein the encircling exterior side surface of the solid core is entirely covered by the shaft between the opposing end faces of the shaft with no slits extending through the shaft to the core.

26. The stabilizing rod as recited in claim 1, wherein for an entire length of the core the fiber encircles the core in a helical pattern and the entire encircling exterior side surface of the core is completely covered by the shaft with no slits extending through the shaft to the core.

27. The stabilizing rod as recited in claim 1, wherein the matrix of fiber and adhesive wound around the core forms a portion of the shaft that is circumferentially continuous at least at the given length of the core completely covered by the shaft.

28. The stabilizing rod as recited in claim 1, wherein for at least portions of the core, the encircling exterior side surface of the core is covered by the two or more overlapping layers of the fibers.

29. The stabilizing rod as recited in claim 1, wherein the section of the shaft that extends continuously as a unitary bonded structure between the opposing end faces of the shaft without encircling the core extends linearly between the opposing end faces of the shaft.

30. A stabilizing rod for use in positioning adjacent vertebrae with respect to each other, the stabilizing rod comprising:

an elongate shaft extending longitudinally between a proximal end and an opposing distal end, the shaft bounding and completely encircling a passageway at least partially extending between the proximal end and the distal end, the shaft being comprised of a radiolucent material, the radiolucent material comprising a matrix of fiber and adhesive; and a solid core having an encircling exterior side surface that extends between opposing end faces, the solid core being disposed within the passageway of the shaft and extending between the proximal and distal ends of the shaft, the solid core having the configuration of a rod and being configured so that the entire length of the core is disposed within a plane, the core being comprised of a radiopaque material and being bonded to the shaft by the adhesive of the shaft along the entire length of the core, the core being the only rod secured to the shaft, wherein the matrix of fiber and adhesive is wound around the core so that the fiber encircles the core in a helical pattern, wherein the matrix of fiber and adhesive is bonded together so that at least a section of the shaft extends continuously as a unitary bonded structure between the proximal end and the opposing distal end of the shaft without encircling the core.

31. A stabilizing rod for use in positioning adjacent vertebrae with respect to each other, the stabilizing rod comprising:

an elongate shaft having a central longitudinal axis extending between a proximal end and an opposing distal end, the shaft bounding and completely encircling a passageway that extends along the central longitudinal axis at least partially between the proximal end and the distal end so that the central longitudinal axis is disposed within the passageway, the shaft being comprised of a radiolucent material, the radiolucent material comprising a matrix of fiber and adhesive; and a solid core disposed within the passageway of the shaft and extending between the proximal and distal ends of the shaft, the solid core being comprised of a radiopaque material such that when the stabilizing rod is X-rayed, the solid core is the only portion of the stabilizing rod viewable on the corresponding X-ray image, the core having an encircling exterior side surface extending along the length thereof that is bonded to the shaft by the adhesive of the shaft along the entire length of the core, wherein the matrix of fiber and adhesive is wound around the core so that the fiber encircles the core along the length thereof in a helical pattern, wherein the matrix of fiber and adhesive is bonded together so that at least a section of the shaft extends continuously as a unitary bonded structure between the proximal end and the opposing distal end of the shaft without encircling the core.

* * * * *

UNITED STATES PATENT AND TRADEMARK OFFICE
CERTIFICATE OF CORRECTION

| | | |
|---|---|---|
| PATENT NO. | : 9,433,439 B2 | Page 1 of 1 |
| APPLICATION NO. | : 12/557081 | |
| DATED | : September 6, 2016 | |
| INVENTOR(S) | : Felix et al. | |

It is certified that error appears in the above-identified patent and that said Letters Patent is hereby corrected as shown below:

In the Specification

Column 6
Line 16, insert --.-- after "formed on alignment cap 250"

Column 9
Line 54, change "By way example and not" to --By way of example and not--

Signed and Sealed this
Third Day of January, 2017

Michelle K. Lee
*Director of the United States Patent and Trademark Office*